United States Patent [19]

Suzuki

[11] Patent Number: 5,747,669
[45] Date of Patent: May 5, 1998

[54] OXYGEN ELECTRODE AND ITS MANUFACTURE

[75] Inventor: Hiroaki Suzuki, Tsukuba, Japan

[73] Assignee: Fujitsu Limited, Kawasaki, Japan

[21] Appl. No.: 733,929

[22] Filed: Oct. 18, 1996

[30] Foreign Application Priority Data

Dec. 28, 1995 [JP] Japan ................. 7-342269
Sep. 4, 1996 [JP] Japan ................. 8-234415

[51] Int. Cl.⁶ ............... G01N 27/04; G01N 27/12; H05B 03/06; A61B 05/00
[52] U.S. Cl. ............ 73/23.21; 73/23.31; 204/410; 204/424; 422/83; 422/94
[58] Field of Search ............... 73/23.31, 31.06; 204/410, 424; 422/83, 94

[56] References Cited

U.S. PATENT DOCUMENTS

| | | | |
|---|---|---|---|
| 4,224,280 | 9/1980 | Takahama et al. | 422/98 |
| 4,311,151 | 1/1982 | Hagihara | 128/635 |
| 4,453,397 | 6/1984 | Ohta et al. | 73/23 |
| 4,697,165 | 9/1987 | Ishiguro et al. | 338/34 |
| 4,772,376 | 9/1988 | Yukawa et al. | 204/410 |
| 4,883,947 | 11/1989 | Murase et al. | 219/553 |
| 4,967,589 | 11/1990 | Yagawara et al. | 73/23.25 |
| 5,250,170 | 10/1993 | Yagawara et al. | 204/431 |
| 5,476,001 | 12/1995 | Hoetzel et al. | 72/23.31 |
| 5,538,620 | 7/1996 | Nikolskaja | 205/782 |
| 5,608,154 | 3/1997 | Kato et al. | 73/23.31 |

FOREIGN PATENT DOCUMENTS

| | | |
|---|---|---|
| 63-238548 | 10/1988 | Japan . |
| 63-238549 | 10/1988 | Japan . |
| 4-125462 | 4/1992 | Japan . |
| 5-87766 | 4/1993 | Japan . |
| 6-34596 | 2/1994 | Japan . |

Primary Examiner—Hezron E. Williams
Assistant Examiner—J. David Wiggins
Attorney, Agent, or Firm—Armstrong, Westerman, Hattori, McLeland & Naughton

[57] ABSTRACT

An oxygen electrode having: an electrode substrate; a first electrode and a first lead wire formed on the electrode substrate; an insulating layer formed on the electrode substrate covering the first lead wire; a second electrode and a second lead wire formed on the electrode substrate, and on the insulating layer; a container substrate bonded to the electrode substrate, and having a first recess with an opening over the first and second electrodes for containing electrolyte; and an oxygen permeable film covering the opening. The oxygen electrode may be provided with lead plates and partially molded in an insulating and fixing resin. An oxygen electrode for measuring an oxygen concentration having a novel structure is provided which can be made more compact and/or be used more easily.

39 Claims, 31 Drawing Sheets

FIG. 12A
FIG. 12B
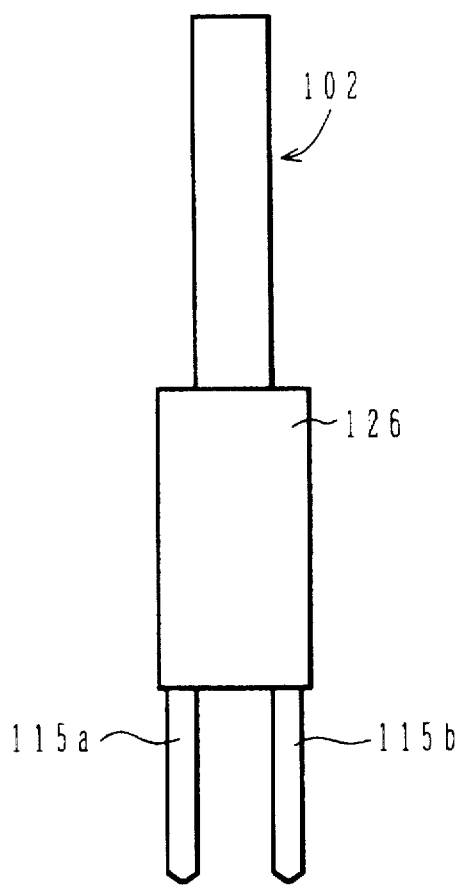
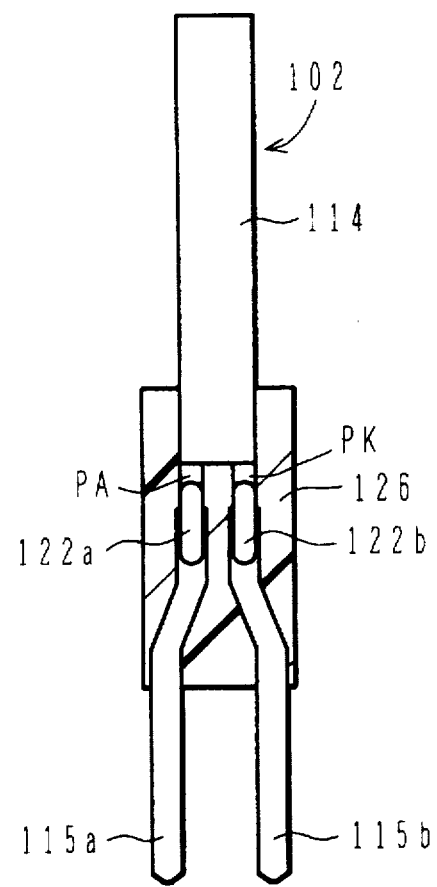

FIG. 20A
FIG. 20B
FIG. 20C
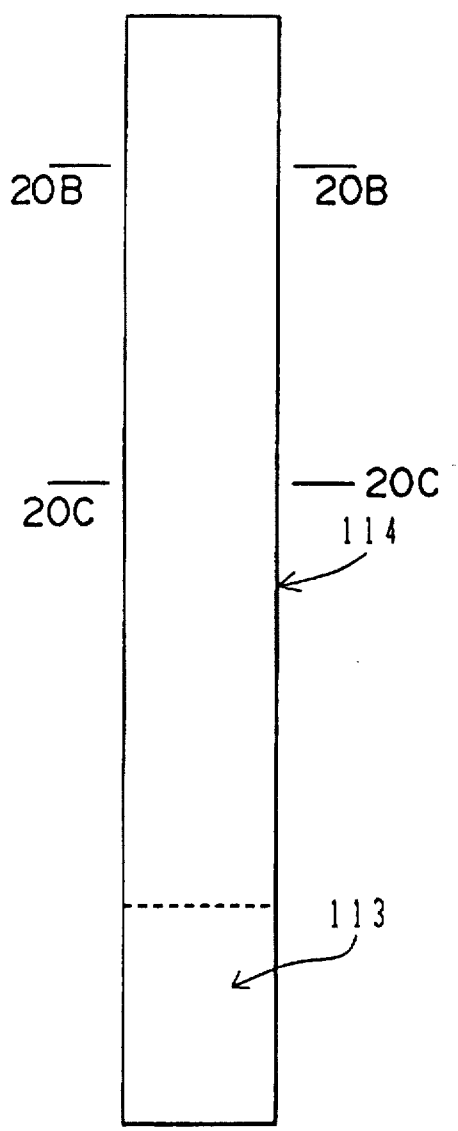
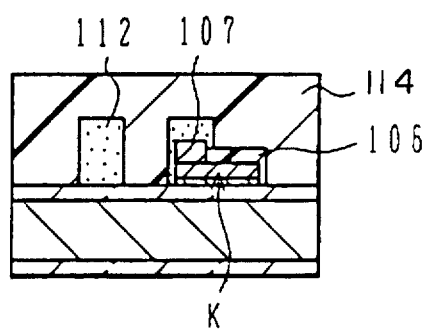
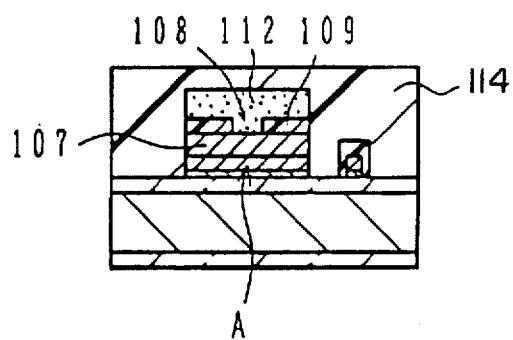

FIG. 24A
FIG. 24B
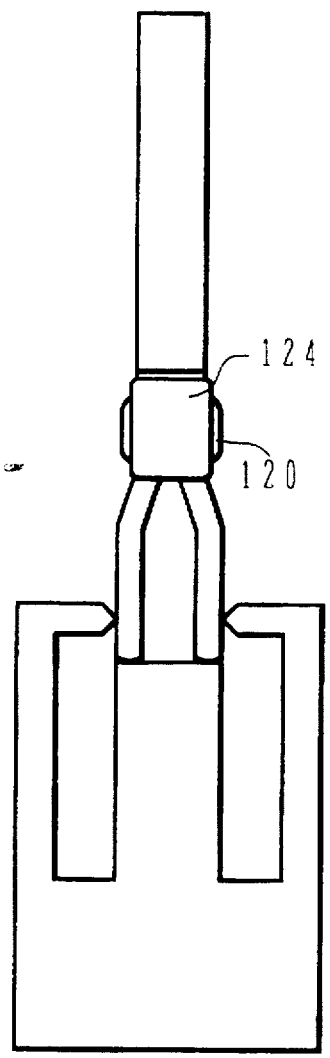
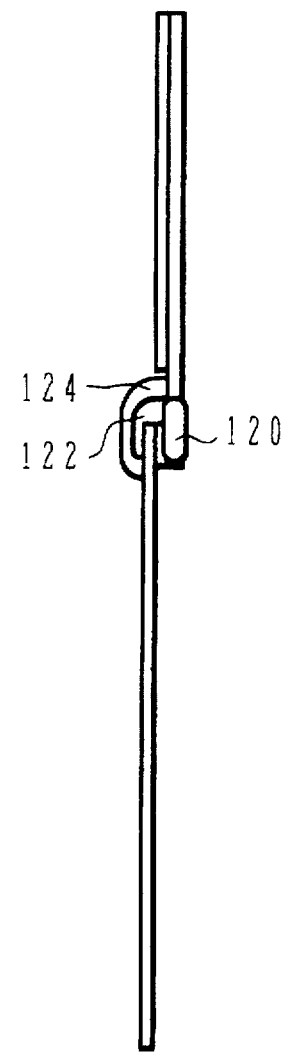

FIG. 25A
FIG. 25B
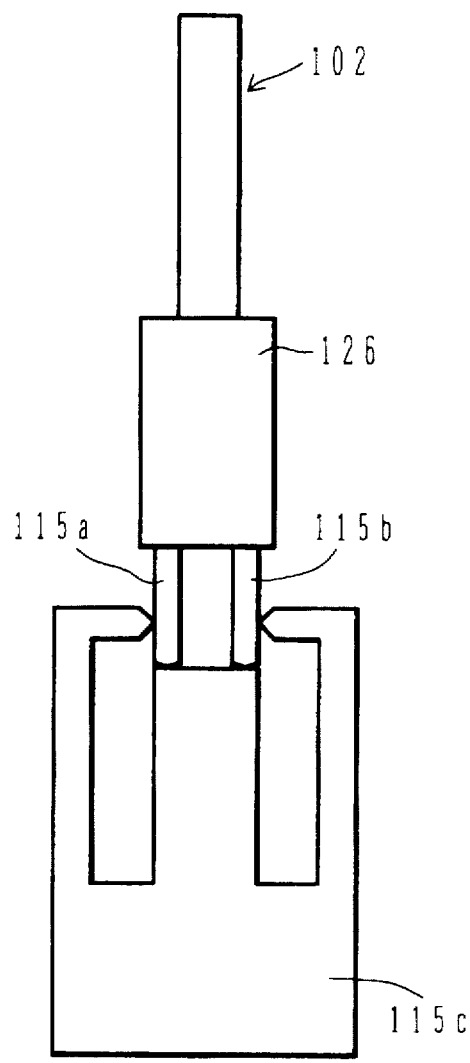
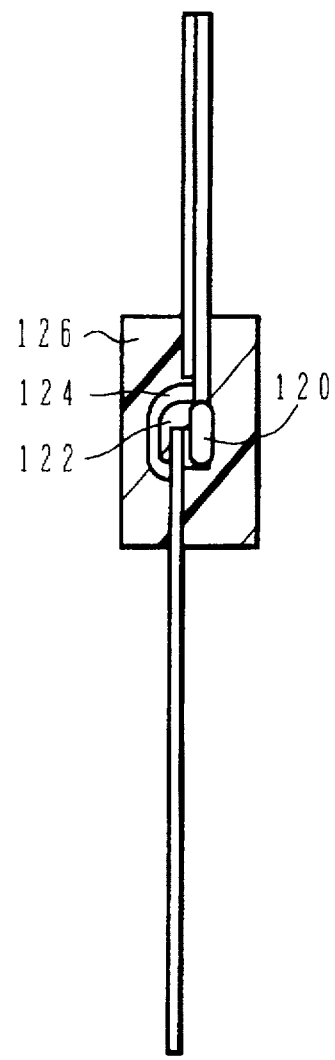

FIG. 30A
FIG. 30B
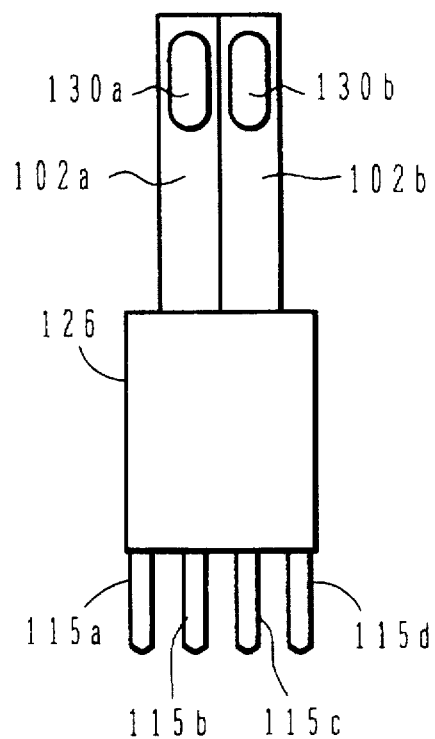
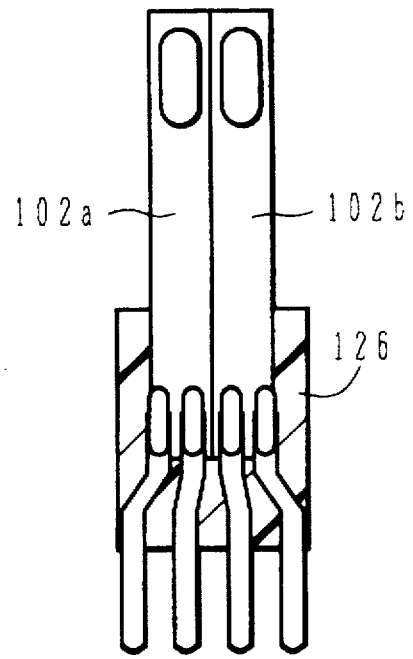

OXYGEN ELECTRODE AND ITS MANUFACTURE

BACKGROUND OF THE INVENTION a) Field of the Invention

The present invention relates to an oxygen electrode for measuring an oxygen concentration, and more particularly to an oxygen electrode for measuring an oxygen concentration which is suitable for miniaturization and/or easy to use.

b) Description of the Related Art

An oxygen electrode is used in various fields for the measurement of a concentration of oxygen dissolved in liquid. For example, for the purpose of water quality maintenance, biochemical oxygen demand (BOD) of water is measured. The dissolved oxygen concentration can be measured with an oxygen electrode. In the field of fermentation industries, it is desired to regulate the dissolved oxygen concentration in a fermenter in order to efficiently promote fermentation. For the measurement of this dissolved oxygen concentration, an oxygen electrode can be utilized.

If immobilized enzymes are used with an oxygen electrode, a biosensor can be formed. Such a biosensor can be used for the measurement of a concentration of sugar, alcohol, or the like. For example, by using immobilized enzymes such as glucose oxidase with an oxygen electrode, a glucose concentration can be measured. Glucose reacts with dissolved oxygen under the catalyzer of glucose oxidase, and generates gluconolactone. Since the amount of dissolved oxygen diffused in an oxygen electrode cell reduces, the glucose concentration can be measured on the basis of a consumption amount of dissolved oxygen. Oxygen electrodes can be used therefore in various fields such as environment measurements, fermentation industries, and clinical treatments.

In the field of clinical treatments in particular, an oxygen electrode is mounted on a catheter and inserted in a body for measurements. For such applications, it is desired that an oxygen electrode is compact, low cost, and disposable.

Conventional oxygen electrodes have been fabricated on a substrate of glass or vinyl chloride. These oxygen electrodes are difficult to be made compact and are not suitable for mass production. The present inventors have proposed a compact oxygen electrode of a new type which is manufactured by utilizing lithography and anisotropic etching (JP-A-63-238549). This oxygen electrode has a structure with a recess that is formed in a silicon substrate through anisotropic etching, two electrodes with an insulating film interposed therebetween are mounted, electrolyte containing solution is introduced in the recess, and lastly the upper surface of the oxygen electrode is covered with a gas permeable film.

The present inventors have also proposed a technology by which an electrolyte layer and a gas permeable film are formed only at necessary areas by means of screen printing (JP-A-5-87766). This oxygen electrode is compact, has less variation in its characteristics, and can manufacture with low cost because of a capability of mass production. The present inventors have also proposed a compact oxygen electrode more suitable for mass production and with higher quality by using a combination of anisotropic etching and anodic bonding (JP-A-4-125462).

Even with these conventional techniques, it is not easy to manufacture an oxygen electrode suitable for being mounted on a catheter and easy to be inserted in a body. In the field of clinical treatments, it is desired to make an oxygen electrode as small as possible.

In a conventional oxygen electrode, wiring patterns for interconnection between electrodes, lead wires, pads, and the like are juxtaposed parallelly on the same plane. In many cases, this arrangement does not pose practical problems, but spaces required for lead wires and the like cannot be neglected if the oxygen electrode is to be minimized more.

In the case of an oxygen electrode used in contact with liquid, it is almost impossible from the following reason to set the distance between lead wires to about 1 μm as in the case of semiconductor ICs. In an oxygen electrode whose cathode and anode contact electrolyte contained therein, if the distance between lead wires is made too short and if, for example, the gas permeable film is accidentally peeled off, the electrolyte percolates to the lead wire region and allows reaction to proceed. In order to increase product reliability, the wiring patterns including lead wires are required to be spaced apart by 100 to 200 μm or more. However, this space becomes a critical issue if an oxygen electrode having a width of 1 mm or less at the top portion is to be manufactured.

As above, miniaturization of oxygen electrodes are being made. As the oxygen electrode is made more compact, new problems have become conspicuous. As the oxygen electrode is made compact and the width thereof is narrowed, connection to an external circuit becomes difficult. Furthermore, if the substrate is made of fragile silicon or glass, the connection portion of the oxygen electrode to the external circuit becomes likely to be broken by stress during handling it.

SUMMARY OF THE INVENTION

It is an object of the present invention to provide an oxygen electrode having a novel structure capable of being made more compact.

It is another object of the present invention to provide a manufacture method of an oxygen electrode capable of being made more compact and detecting an oxygen concentration with higher precision.

It is another object of the present invention to provide a compact oxygen electrode easy to use and hard to be broken.

According to one aspect of the present invention, there is provided an oxygen electrode comprising: an electrode substrate for supporting a plurality of electrodes and lead wires connected to the electrodes; a first electrode and a first lead wire connected to the first electrode, the first electrode and the first lead wire being formed on the electrode substrate; an insulating layer formed on the electrode substrate, covering the first lead wire; a second electrode and a second lead wire connected to the second electrode, the second electrode and the second lead wire being formed on the electrode substrate, and on the insulating layer; a container substrate bonded to the electrode substrate, the container substrate having a first recess over the first and second electrodes, the container substrate having an opening in said first recess over at least one of the first and second electrodes; and an oxygen permeable film covering the opening.

The first lead wire (first electrode) and second lead wire (second electrode) are stacked with the insulating layer being interposed therebetween. It is therefore possible to reduce an area necessary for wiring. For example, by laminating the electrode and lead wire, the area necessary for the lead wire can be eliminated.

It is therefore possible to reduce the area necessary for electrodes and lead wires and to make an oxygen electrode or a biosensor more compact.

According to another aspect of the present invention, there is provided an oxygen electrode comprising: an electrode substrate having an insulating surface; a first electrode member formed on the insulating surface of the electrode substrate, the first electrode member including a first electrode, a first lead wire, and a first connection pad electrically connected together; a second electrode member formed on the insulating surface of the electrode substrate, the second electrode member including a second electrode, a second lead wire, and a second connection pad electrically connected together; an electrolyte layer disposed over the electrode substrate so as to form a conductive path between the first and second electrodes; an oxygen permeable film disposed over the electrode substrate, covering the electrolyte layer; first and second lead plates fixed to the electrode substrate; a first connection member for connecting the first connection pad to the first lead plate; a second connection member for connecting the second connection pad to the second lead plate; and an insulating mold member fixed to the electrode substrate and covering the first and second connection pads and parts of the first and second lead plates, and the first and second connection members.

By connecting the lead plate to the connection pad of the electrode substrate, a connection to an external circuit is made easy. By covering the connection pad and lead plate with mold member, an external stress becomes hard to be applied to the electrode substrate so that breakage of the electrode substrate can be prevented.

As above, since the oxygen electrode can be made compact and terminals easy to handle can be protruded to the outside, it is easy to handle the compact oxygen electrode. Similarly, a compact biosensor can be provided which is easy to handle.

BRIEF DESCRIPTION OF THE DRAWINGS

FIGS. 12A and 12B are a plan view and a partially broken plan view showing the structure of an oxygen electrode according to another embodiment of the invention.

FIGS. 13A to 20C are cross sectional views and plan views illustrating the processes of fabricating the compact oxygen electrode shown in FIGS. 12A and 12B.

FIGS. 24A and 24B are a plan view and a side cross sectional view showing the lead frame fixed to a sensor chip in a stabilized electrical connection state.

FIGS. 25A and 25B are a plan view and a side cross sectional view of a configuration in which the connection part of a sensor chip and a lead frame is molded with resin.

FIGS. 30A and 30B are a plan view and a partially broken plan view showing the structure of a biosensor according to another embodiment of the invention.

DETAILED DESCRIPTION OF THE PREFERRED EMBODIMENTS

Figure 1C:
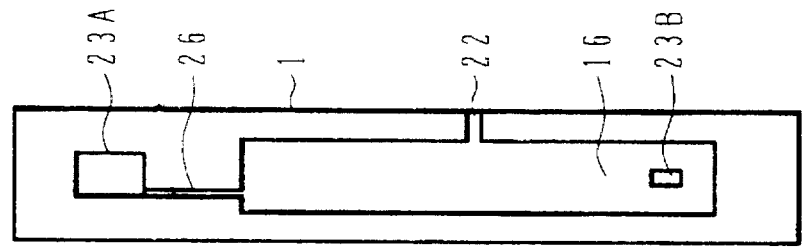
FIGS. 1A to 1C are plan views of an oxygen electrode according to an embodiment of the invention.
Figure 1B:
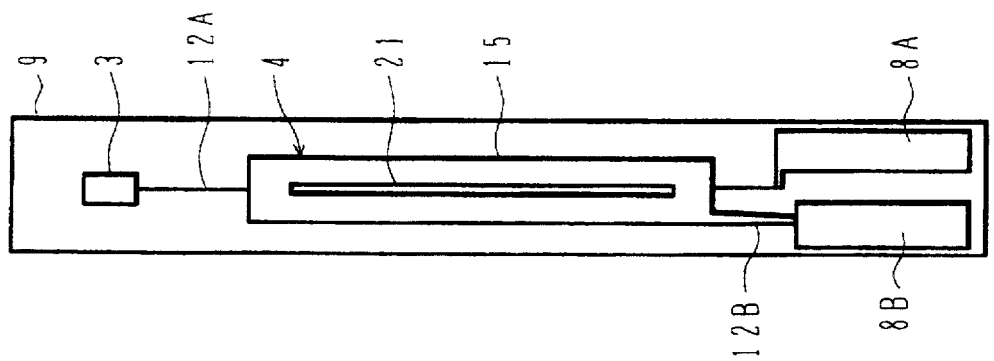
Figure 1A:
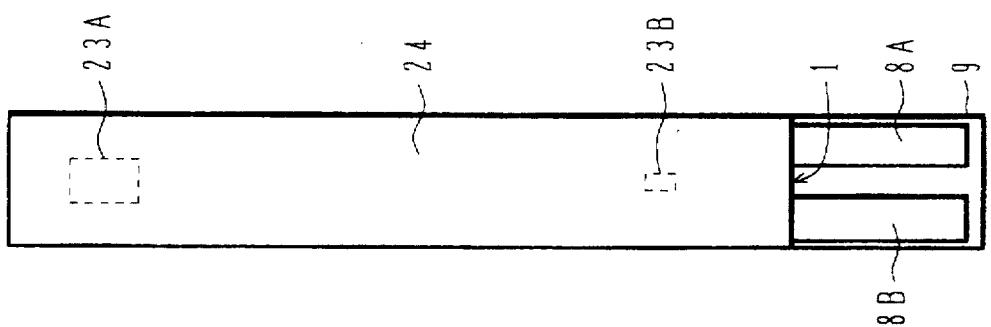

FIGS. 1A to 1C show an oxygen electrode according to an embodiment of the invention. FIG. 1A is a plan view of the oxygen electrode. FIG. 1B shows a lower substrate of the oxygen electrode, and FIG. 1C shows an upper substrate of the oxygen electrode.

As shown in FIG. 1A, electrode pads 8A and 8B are formed on a lower substrate 9 of the oxygen electrode, and exposed to the outside. An upper substrate is bonded to the upper portion of the lower substrate. The surface of the upper substrate 1 is covered with an oxygen permeable film 24 under which through holes 23A and 23B are formed.

FIG. 1B shows the structure of the lower substrate 9. The lower substrate 9 is made of, for example, a glass substrate. On the surface of the lower substrate 9, a cathode 3, a lead wire 12A connected to the cathode 3, and a pad 8A connected to the lead wire 12A are formed. The surface of the lead wire 12A is covered with a polyimide layer on which an anode 4 is formed. The anode 4 and lead wire 12A are electrically insulated by the polyimide layer.

On the surface of the anode 4, a protective layer 15 with a slit opening 21 is formed. The protective layer 15 is formed on almost the whole surface of the anode 4 and exposes the anode 4 only at the central elongated region. The anode 4 is connected via a lead wire 12B to a pad 8B.

On this lower substrate 9, the upper substrate 1 shown in FIG. 1C is bonded. The upper substrate 1 is made of, for example, a silicon substrate, and has the through hole 23A at the area over the cathode 3 and a recess 16 at the area over the anode 4. A through hole 23B is formed in a partial area of the recess 16. The through hole 23A communicates via a narrow long groove 26 with the recess 16.

The volumes (cross section) of the through hole 23A and recess 16 each are much larger than that of the groove 26. An electrolyte inlet port 22 of a groove shape is formed in the side wall of the recess 16.

As the upper substrate shown in FIG. 1C is bonded to the lower substrate shown in FIG. 1B, the oxygen electrode shown in FIG. 1A is completed. Bonding can be efficiently performed, for example, through anodic bonding. Electrolyte is introduced via the inlet port 22 into the through hole 23A, groove 26, and recess 16.

As the oxygen electrode shown in FIG. 1A is immersed in liquid whose oxygen concentration is to be measured, oxygen in the liquid passes through the oxygen permeable film 24, diffuses through the underlying through hole 23A, and reaches the cathode 3. A constant negative voltage is applied to the cathode 3 relative to the anode 4. The amount of current flowing between the anode 4 and cathode 3 is proportional to the oxygen concentration, and is measured.

In the structure shown in FIGS. 1A to 1C, the lead wire 12A of the cathode 3 is insulated by the polyimide film and runs under the anode 4. Namely, the lead wire 12A is disposed between the anode 4 and substrate 9. With this stacked wiring structure, the wiring area in substrate plane dedicated to the lead wire 12A can be dispensed with so that the width of the oxygen electrode can be narrowed.

A manufacture method of the oxygen electrode shown in FIGS. 1A to 1C will be described with reference to FIGS. 2A to 9B.

Figure 2A:
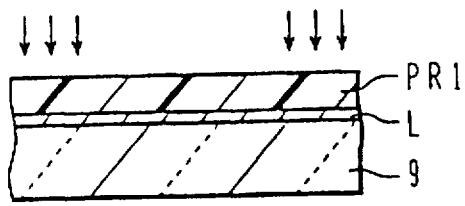
FIGS. 2A to 9B are cross sectional views and plan views illustrating the manufacture method of the oxygen electrode shown in FIGS. 1A to 1C.

As shown in FIG. 2A, a glass substrate 9 having a thickness of, for example, 500 μm is prepared and cleaned with a mixed solution of hydrogen peroxide and ammonium, and with concentrated nitric acid. Glass may be Pyrex glass. If a smaller oxygen electrode is to be formed, a Pyrex glass plate of about 300 μm thick may be used.

In the following description, although only one oxygen electrode is shown, a number of oxygen electrode structures are practically formed on a single wafer at the same time.

Next, a chromium layer L as a tight contact layer is vapor deposited on one surface of the glass substrate 9 to a thickness of 100 nm. A negative type photoresist layer (e.g., OMR-83 (product name), 100 cP, manufactured by Tokyo Ohka Kogyo Co., Ltd.) PR1 is coated on the chromium film L of the glass substrate 9, and thereafter pre-baked for 30 minutes at 80° C. A predetermined area of this photoresist layer PR1 is exposed.

Figure 2B:
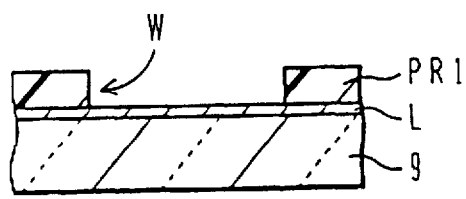

As shown in FIG. 2B, the exposed photoresist film PR1 is developed to form an opening W therein. After the development, the substrate is rinsed and thereafter baked for 30 minutes at 150° C.

Figure 2C:
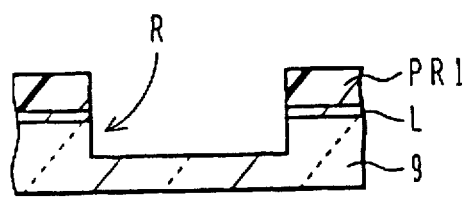

As shown in FIG. 2C, the chromium film L exposed in the opening W is removed. As the etchant for chromium, for example, a solution of NaOH 0.5 g and $K_3Fe(CN)_6$ 1 g mixed with water 4 ml may be used. The substrate is immersed in 50% hydrofluoric acid cooled with ice to etch the glass substrate 9 not covered with the negative type photoresist layer PR1 to thereby form a recess R. The depth of the recess R is, for example, about 9 μm.

Figure 2D:
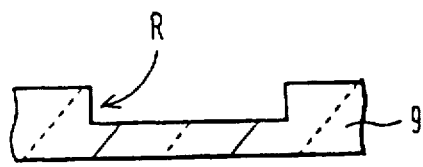

As shown in FIG. 2D, the glass substrate 9 is immersed in a mixed solution of sulfuric acid+hydrogen peroxide=2:1 to remove the negative type photoresist layer PR1. The substrate is then immersed in chromium etchant to remove the chromium film L. The glass substrate with the chromium film L having been removed is cleaned with a heated mixed solution of hydrogen peroxide and ammonium and with pure water, and thereafter dried. In the above manner, the recess R having a predetermined shape is formed on the surface of the glass substrate 9.

Figure 2E:
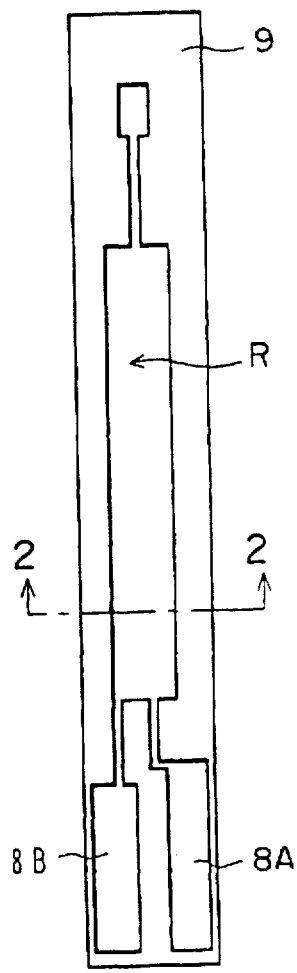

FIG. 2E is a plan view of the lower substrate 9 showing the recess R. The recess R includes a rectangular area for housing the cathode electrode, an elongated area under the rectangular area in the figure for housing the cathode lead wire, and a rectangular area of a relatively large area under the elongated area for housing the anode. In the structure shown in FIG. 2E, elongated areas for housing lead wires and rectangular areas for housing electrode pads are formed, respectively under the rectangular area of a relatively large area. The rectangular recess areas for the electrode pads may not be formed, but the electrode pads may be formed directly on the substrate.

Figure 3A:
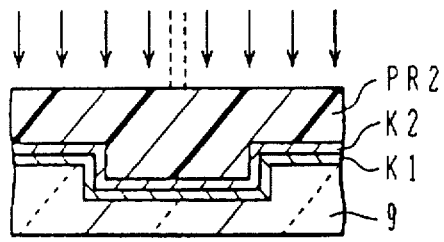

As shown in FIG. 3A, on the surface of the glass substrate 9 formed with the recess R, a chromium layer K1 of 40 nm thick and a gold layer K2 of 150 nm thick are vapor deposited in vacuum in this order. Since the chromium layer is interposed, the gold layer can be formed on the glass substrate in tight contact with the substrate. On the gold layer K2, a positive type photoresist layer (e.g., OFPR-5000 (product name), manufactured by Tokyo Ohka Kogyo Co., Ltd.) PR2 is spin coated, and the substrate is pre-baked for 30 minutes at 80° C. The photoresist layer PR2 formed in the above manner is selectively exposed.

Figure 3F:
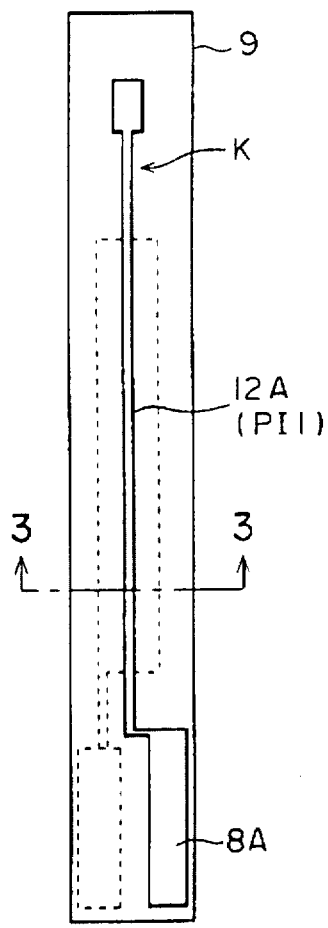
Figure 3B:
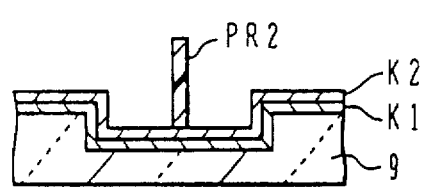
Figure 3C:
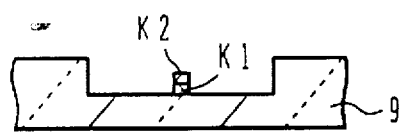

As shown in FIG. 3B, the photoresist layer PR2 is developed to leave only the exposed region which is used as an etching mask for etching the gold layer K2 and chromium layer K1.

The gold layer K2 is etched by etchant of $I_2$ 1 g and KI 4 g dissolved in water 40 ml to remove the gold layer K2 at the area other than under the photoresist pattern PR2. After the resist pattern PR2 is removed, the same chromium etchant is used to remove the exposed chromium film K1.

In the above manner, a cathode pattern is formed which is a laminate of the chromium layer K1 and gold layer K2. This substrate is cleaned with a heated mixed solution of hydrogen peroxide and ammonium and pure water, and thereafter dried.

Figure 3D:
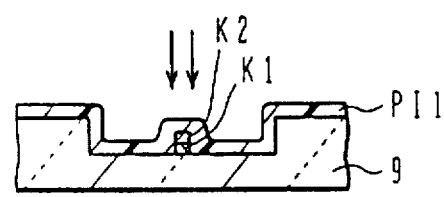

As shown in FIG. 3D, on the glass substrate with the cathode pattern, photosensitive polyimide source liquid (Photoneece (product name UR-3140), manufactured by Toray Industries Inc.) is spin coated to form a polyimide layer PI1. For example, after spin coating at a revolution speed of 1200 rpm for 30 seconds is performed, spin coating at a revolution speed of 2000 rpm for 2 seconds is performed. Thereafter, the polyimide layer PI1 is pre-baked for 90 minutes at 80° C.

A pattern corresponding to the lead wire of the cathode pattern is exposed onto the photosensitive polyimide layer PI1.

Figure 3E:
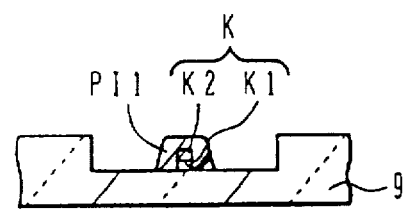

As shown in FIG. 3E, the polyimide layer PI1 is developed with developing liquid (e.g., DV-605 (product name), manufactured by Toray Industries Inc.), and the substrate is rinsed three times in isopropyl alcohol. In the above manner, the undeveloped polyimide layer is removed.

FIG. 3F is a schematic diagram showing the structure of the lower substrate formed by the above processes. The laminate of the chromium layer and gold layer is formed at the area corresponding to the cathode pattern in the recess formed in the glass substrate 9, and part of the lead at the central area is further stacked with the polyimide layer PI1. In the structure of the cathode pattern, the cathode electrode 3 is connected via the lead wire 12A to the electrode pad 8A.

As shown in FIG. 3E, in order to reliably cover the surface and side wall of the cathode lead wire 12A with the polyimide layer PI1, it is preferable to use an exposure pattern for the polyimide layer slightly wider than that for the gold layer and chromium layer.

The polyimide pattern PI1 is cured by baking it for 30 minutes at 150° C., for 30 minutes at 200° C., and for 1 hour at 300° C.

Instead of polyimide, negative type photoresist may be used. If the negative type photoresist is used as an interlayer insulating film, processes similar to those in FIGS. 2A and 2B are performed for the lead wire of the cathode.

Figure 4A:
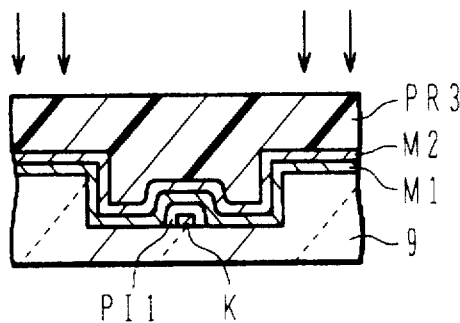

As shown in FIG. 4A, on the surface of the glass substrate 9 formed with the cathode pattern, a chromium layer M1 of 40 nm thick and a gold layer M2 of 150 nm thick are vapor deposited in vacuum in this order. On the gold layer M2, a positive type photoresist layer (e.g., OFPR-5000 (product name), manufactured by Tokyo Ohka Kogyo Co., Ltd.) PR3 is spin coated, and pre-baked for 30 minutes at 80° C. The photoresist layer PR3 is then selectively exposed.

Figure 4B:
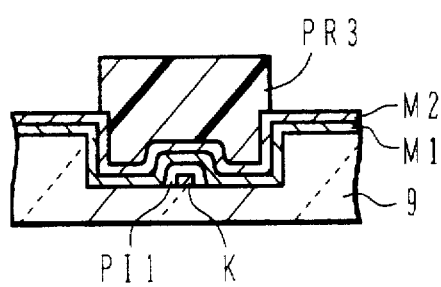
Figure 4C:
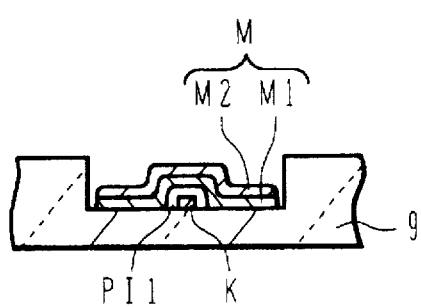

As shown in FIG. 4B, the exposed photoresist layer PR3 is developed to form an etching mask PR3 exposing the area other than the anode pattern. As shown in FIG. 4C, by using the resist mask PR3 as an etching mask, the exposed gold layer M2 and chromium layer M1 are etched by the above-described etchant for the gold layer and chromium layer. Thereafter, the substrate is cleaned and dried and the left photoresist pattern is removed with acetone.

Figure 4D:
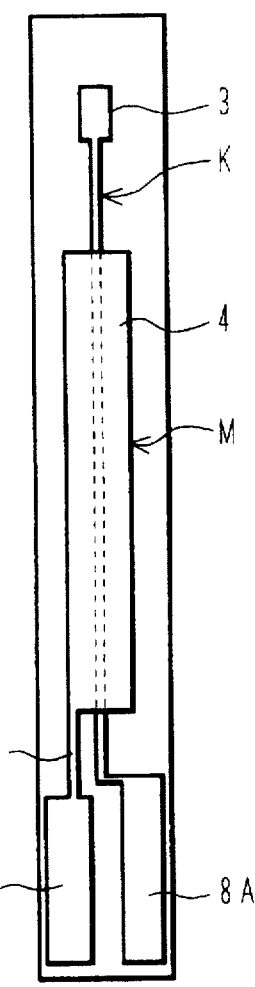

FIG. 4D is a plan view showing the anode pattern M having the anode electrode 4, lead wire 12B, and electrode pad 8B.

The cathode pattern K and anode pattern M are accommodated in the recess R formed in the substrate at the level lower than the surface of the glass substrate 9. Therefore, when the glass substrate 9 is bonded to another flat surface, the anode pattern and cathode pattern do not hinder bonding.

Figure 5A:
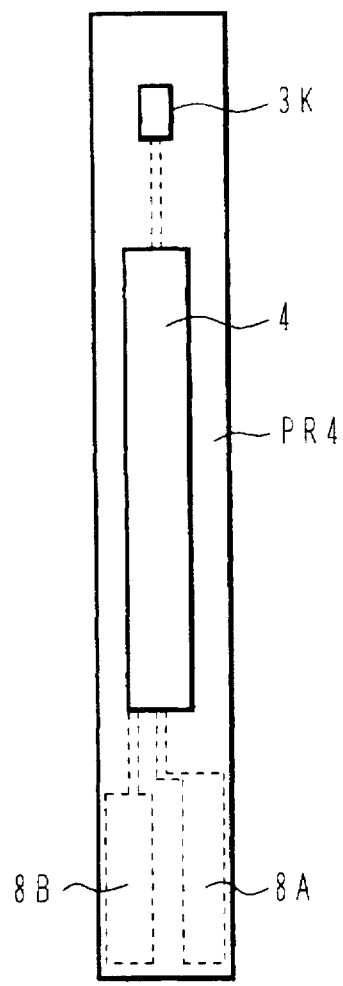

As shown in FIG. 5A, on the glass substrate 9, a positive type photoresist layer (e.g., OFPR-5000 (product name), manufactured by Tokyo Ohka Kogyo Co., Ltd.) PR4 is spin coated, and pre-baked for 30 minutes at 80° C. Thereafter, the photoresist layer PR4 is exposed using a pattern with openings corresponding to the cathode electrode 3 and anode electrode 4, and the substrate is immersed in toluene for 10 minutes at 30° C. and baked for 15 minutes at 80° C. Thereafter, the photoresist layer PR4 is developed to form a photoresist pattern PR4 exposing the sensing areas corresponding to the cathode electrode 3 and anode electrode 4.

Figure 5C:
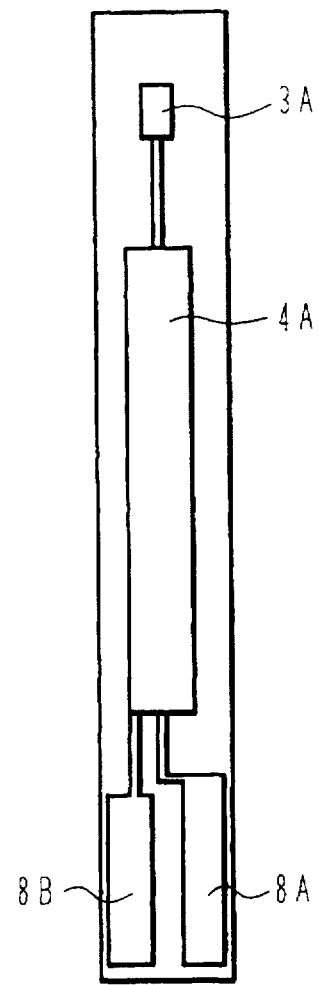
Figure 5B:
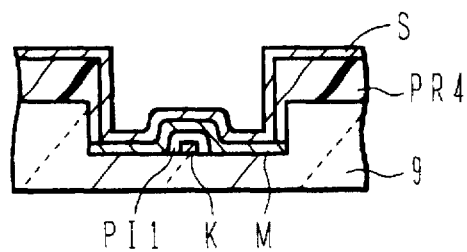
Figure 5D:
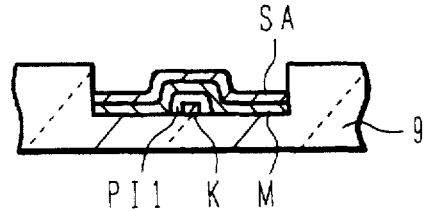

As shown in FIG. 5B, on the glass substrate formed with the resist pattern, a silver film S is vapor deposited. Thereafter, the resist pattern PR4 is removed with acetone to lift off the silver film S formed thereon About—1.0 V is applied for 1 minute to the cathode in 0.1M KCl solution to form silver chloride on the anode. The glass substrate with the silver chloride layer SA formed on the surface of an anode electrode 4A is thus formed as shown in FIGS. 5C and 5D. FIG. 5C is a plan view and FIG. 5D is a cross sectional view.

Figure 6A:
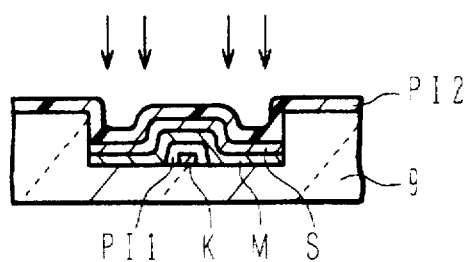

As shown in FIG. 6A, on the surface of the glass substrate, polyimide source liquid is spin coated to form a polyimide layer PI2. Spin coating is performed, for example, at a revolution speed of 2300 rpm for 30 seconds. After spin coating the polyimide layer, the polyimide layer is pre-baked for 90 minutes at 80° C. Thereafter, the polyimide film PI2 is selectively exposed in the manner described above.

Figure 6C:
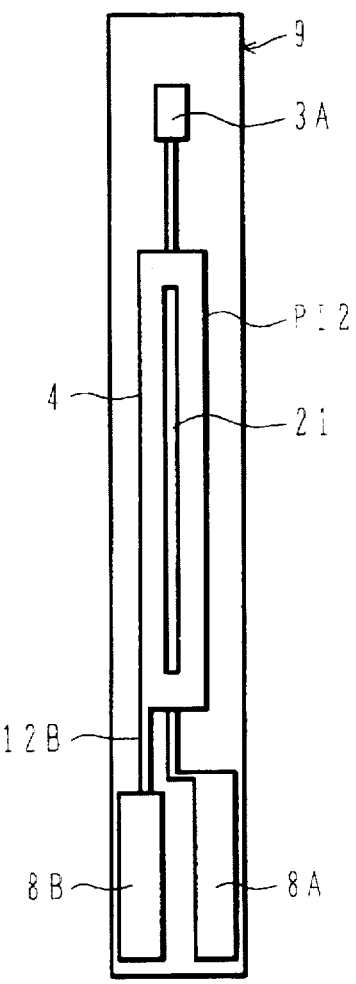
Figure 6B:
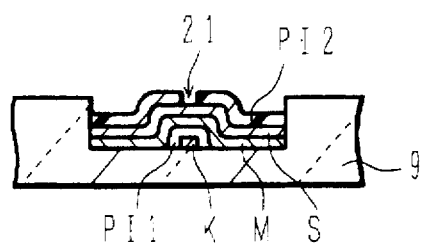

As shown in FIG. 6B, the exposed polyimide film is developed to form a polyimide pattern PI2 having an elongated window exposing the central area of the anode electrode in a slit shape. The polyimide pattern is then cured for 30 minutes at 150° C., for 30 minutes at 200° C., and for 1 hour at 300° C.

FIG. 6C shows the shape of the polyimide pattern PI2 formed in the above manner. The polyimide pattern PI2 covers the anode electrode 4 and lead wire 12B and provides an opening 21 of a slit shape to expose the central area of the anode electrode. Instead of polyimide, negative type photoresist may be used. The negative type photoresist has a water repellent nature.

The polyimide pattern exposing only the central area of the anode electrode and covering the other area is effective for reducing an initial operation stabilizing time by restricting the area of the exposed silver chloride layer and effective for prolonging a life time of the oxygen electrode. The number of slits 21 is not limited to one. Two or more slits may be formed if the conductance between the electrodes is not sufficient and is to be increased.

In the above manner, the glass substrate supporting the electrodes is formed. Next, a silicon substrate covering the electrode substrate will be described.

Figure 7A:
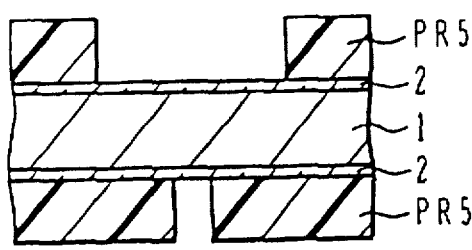

As shown in FIG. 7A, a silicon substrate 1 of 400 μm thick having the (1 0 0) plane is prepared and cleaned with a mixed solution of hydrogen peroxide and ammonium, and with concentrated nitric acid. If a smaller oxygen electrode is to be formed, a thinner silicon substrate is used, for example, about 150 μm thick. Similar to the electrode substrate, in the following description, although only one oxygen electrode is shown, a number of oxygen electrode structures are practically formed on a single wafer at the same time.

The cleaned silicon substrate is wet oxidized for about 200 minutes at 1000° C. to form $SiO_2$ insulating films 2 of about 1.0 μm thick on both surfaces of the substrate. On both the surfaces of the silicon substrate 1, a negative type photoresist layer (e.g., OMR-83 (product name), manufactured by Tokyo Ohka Kogyo Co., Ltd.) PR5 is spin coated and pre-baked for 30 minutes at 80° C. This photoresist layer PR5 is exposed with a predetermined pattern, developed, and rinsed. The photoresist pattern PR5 formed on the upper surface of the silicon substrate 1 has an opening conformal to the recess 16 into which electrolyte is introduced over the glass substrate, and the photoresist pattern PR5 formed on the lower surface of the silicon substrate 1 has an opening at the area corresponding to the through hole 23. This resist pattern is baked for 30 minutes at 150° C.

Figure 7C:
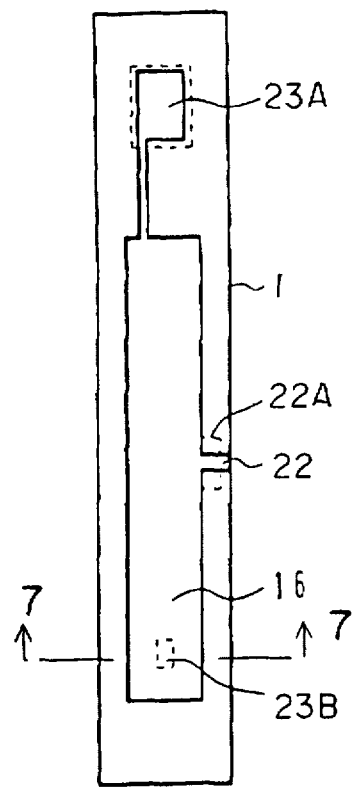
Figure 7B:
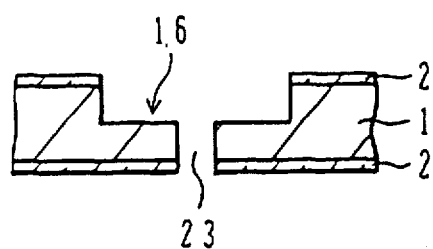

As shown in FIG. 7B, by using the resist pattern as an etching mask, the exposed $SiO_2$ is etched and removed. This etching is performed, for example, by immersing the silicon substrate 1 in a solution of 50% hydrofluoric acid:40% ammonium fluoride=1:6 to etch $SiO_2$ not covered with the photoresist. The substrate with the $SiO_2$ films removed is immersed in a mixed solution of sulfuric acid:hydrogen peroxide=2:1 to remove the negative type photoresist film PR5.

The silicon substrate 1 with the photoresist layer being removed is immersed in aqueous solution of 35% potassium hydroxide for 1 hour to anisotropically etch the silicon substrate not covered with the $SiO_2$ film 2. When the recess 16 etched from the front surface and the through hole 23 etched from the back surface communicate with each other, the etching is stopped.

In the above manner, the silicon substrate shown in FIG. 7C is obtained. As shown, the portion interconnecting the cathode electrode and anode electrode is preferably formed in a narrow groove. If the cross sectional areas are set as above, the influence of by-products generated at the electrodes can be suppressed.

It is preferable to form an electrolyte inlet port by forming another groove 22 as shown in the right hand side of the substrate in FIG. 7C, extending from the anode electrode to the side wall of the substrate. The electrolyte inlet port is desired to be disposed apart from the sensing region of the oxygen electrode. Although this electrolyte inlet port extends from the anode electrode to the side wall of the substrate, it may be a through hole reaching the back surface of the substrate.

The through hole 23B under the anode electrode region functions as an air drain hole. Although this air drain hole may be omitted, it makes it easy to introduce electrolyte.

The silicon substrate 1 anisotropically etched in the above manner, is cleansed with a mixed solution of hydrogen peroxide and ammonium and with concentrated nitric acid.

Figure 8A:
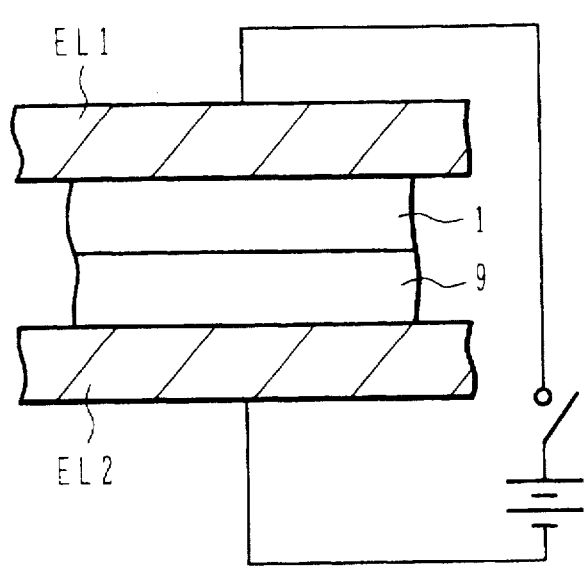

The glass substrate 9 with the electrode patterns and the silicon substrate 1 with the recess are immersed in pure water and cleaned with ultrasonic wave for 10 minutes. As shown in FIG. 8A, the substrates 1 and 9 are superposed and placed between anodic boding electrodes EL1 and EL2. A voltage of 1200 V is applied across the electrodes EL1 and EL2 with the glass substrate 9 being set negative, in a nitrogen atmosphere at 250° C., to anodically bond the glass substrate 9 and silicon substrate 1 together. Anodic bonding is possible between a silicon substrate and a glass substrate, or between silicon substrates. If an $SiO_2$ layer is formed on the silicon substrate, this substrate is treated same as the glass substrate.

Figure 8B:
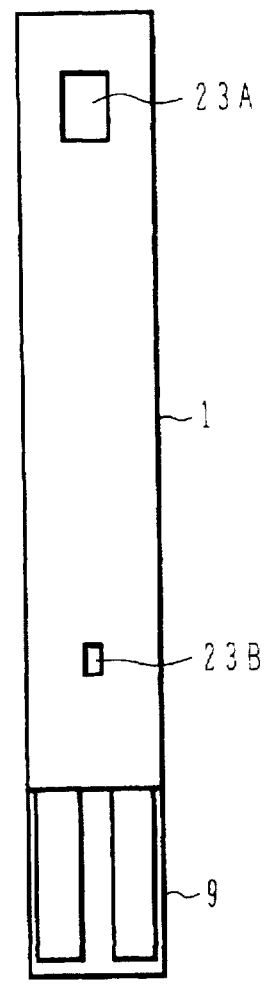

As shown in FIG. 8B, the silicon substrate 1 is tightly bonded to the glass substrate 9 through anodic bonding. The through hole 23B for air drain and the through hole 23A for oxygen permeation are being formed in the silicon substrate 1.

Instead of anodic bonding, two substrates may be bonded with adhesive, or by using substance which dissolves at least one of the substrates.

Figure 8C:
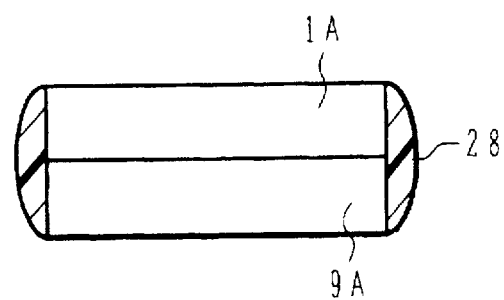

FIG. 8C illustrates such bonding processes. Adhesive 28 is coated on the side walls of superposed substrates 1A and 9A. The adhesive 28 is preferably creeps between the substrates 1A and 9A to bond the opposing surfaces of the substrates. Instead of adhesive, substance which dissolves at least one substrate may be used.

Figure 9A:
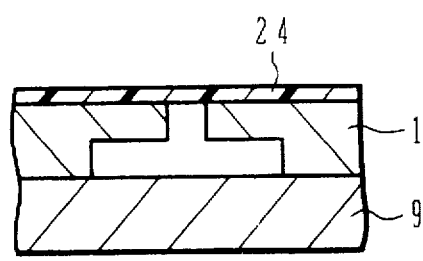

As shown in FIG. 9A, a gas permeable film 24 is covered on the back surface (upper surface as viewed in FIG. 9A) of the silicon substrate 1 adhered to the glass substrate 9. For example, an FEP film (manufactured by Toray Industries Inc. and having a thickness of 12 μm) is applied on an area at least covering the opening of the sensing region, or may be applied over the whole back surface of the silicon substrate.

Figure 9B:
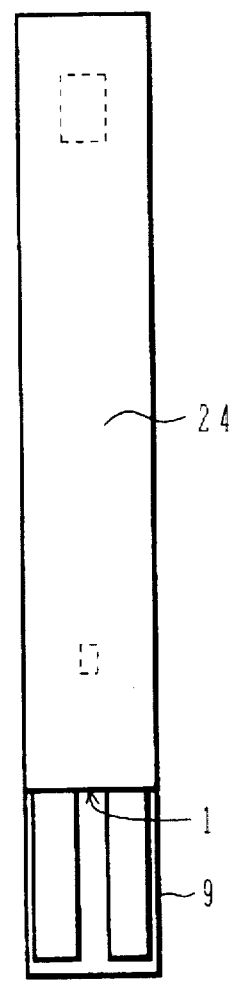

As shown in FIG. 9B, the laminated substrate is cut into each chip with a dicing saw to complete each oxygen electrode.

The oxygen electrode structure formed by the above processes is immersed in electrolyte (e.g., 0.1M KCl solution) and the pressure of the space including the electrolyte is reduced. As the pressure of the space above the electrolyte is reduced, air in the oxygen electrode structure moves to the outside whereas the electrolyte is introduced into the space in the oxygen electrode structure. If an air drain hole is provided, the pressure of the space is reduced while the air drain hole is exposed in the vapor phase so that the electrolyte can be introduced more efficiently. With the introduced electrolyte, the oxygen electrode provides a function of sensing an oxygen concentration.

The structure of the oxygen electrode is not limited to the above embodiment.

Figure 10A:
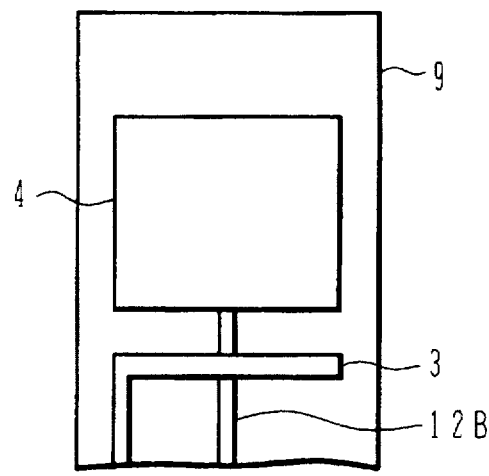
FIGS. 10A to 10C are plan views of modifications of the oxygen electrode shown in FIGS. 1A to 1C.
Figure 10B:
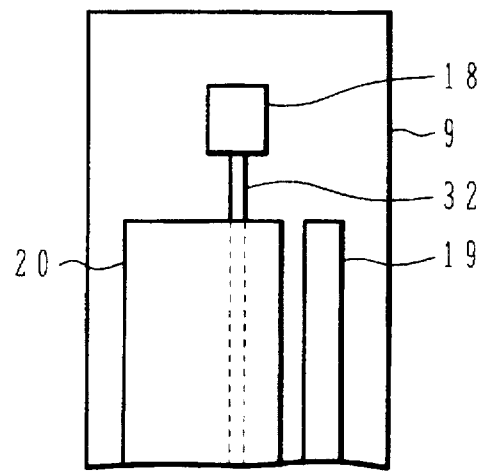
Figure 10C:
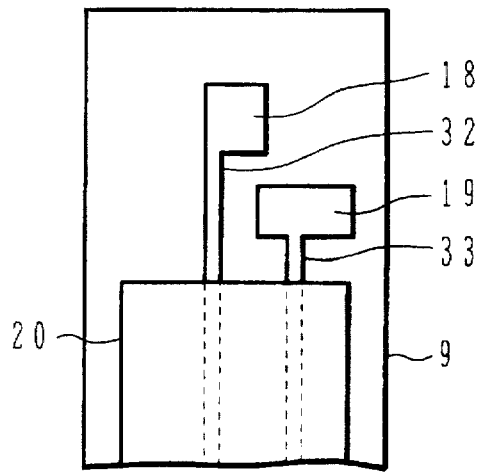

FIGS. 10A to 10C shows examples of other structures of the oxygen electrodes. In FIG. 10A, an anode electrode 4 is formed at the distal end portion of the glass substrate 9, and a lead wire 12B of the anode electrode is disposed under a cathode electrode 3. An insulating layer is coated on the surface of the lead wire 12B to electrically isolate the cathode 3 and lead wire 12B. Namely, the anode lead wire 12B is disposed between the cathode pattern 3 and substrate 9.

An oxygen electrode of a three-electrode structure is preferable for achieving precise electrochemical measurement of an oxygen concentration. FIGS. 10B and 10C show the structures of oxygen electrodes of the three-electrode structure.

In FIG. 10B, a reaction electrode (cathode) 18 is disposed at the distal end portion of the glass substrate 9, and an opposing electrode (anode) 20 and a reference electrode 19 are juxtaposed below the reaction electrode 18 in the figure. A lead wire 32 of the reaction electrode 18 is covered with an insulating film and disposed under the opposing electrode 20. The lead wire 32 covered with the insulating layer is disposed between opposing electrode 20 and substrate 9. The reference electrode 19 is made of a laminate of a chromium layer and a gold layer and a silver layer. Although a voltage is applied to the reference electrode, current will not flow through this reference electrode.

As shown in FIG. 10C, a lead wire 33 of the reference electrode 19 may also be disposed under the opposing electrode 20. The lead wires 32 and 33, covered with the insulating film, of the reaction electrode 18 and reference electrode 19 are disposed between the opposing electrode 20 and substrate 9.

For the three-electrode structure, a silver layer is formed on the surface of the reaction and reference electrodes, and a gold layer itself is left on the surface of the opposing electrode 20.

It is preferable for the three-electrode structure to form three recesses for the three electrodes and to connect these recesses by narrow grooves. The reference electrode is not necessarily required to be connected to the opposing electrode. In this case, electrolyte input ports are preferably formed at locations near the reference and opposing electrodes. An additional air drain hole may be formed. If one electrolyte inlet port is formed for each of the reference and opposing electrodes, one of the ports may be used for the air drain hole.

If immobilized bio-substance is used with such an oxygen electrode, a biosensor can be formed.

Figure 11A:
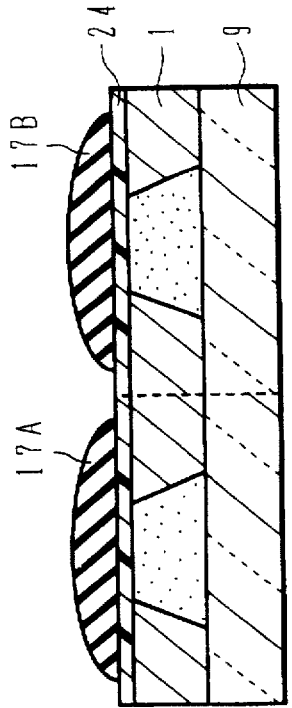
FIGS. 11A to 11D are schematic cross sectional views showing the structures of biosensors according to other embodiments of the invention.

FIG. 11A shows a structure that an immobilizing film 17 is formed on the surface of an FEP film 24 coated on the surface of a silicon substrate 1. The immobilizing film 17 immobilizes enzymes such as glucose oxidase. This immobilizing film 17 may be formed, for example, by immersing a compact oxygen electrode sensing portion (portion including the cathode electrode and its corresponding through hole) in a solution of glucose oxidase 1mg dissolved in a solution of 20 ml of bovine serum albumin 5 wt % and glutaraldehyde 5 wt %, and by drying it.

Figure 11C:
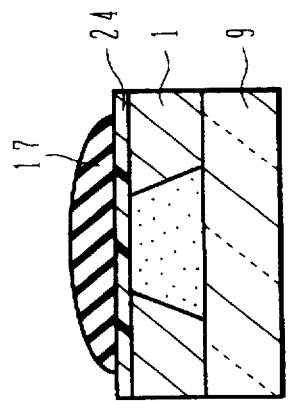
Figure 11B:
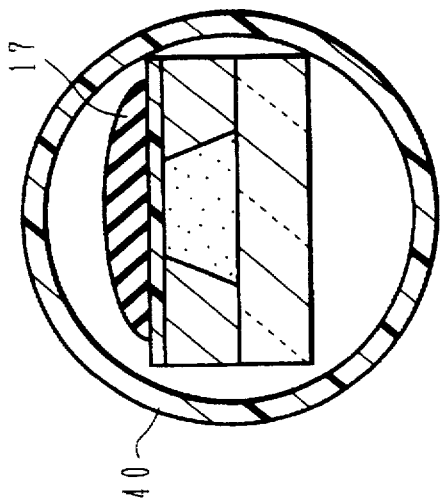

As shown in FIG. 11B, a plural type of biosensor may be formed by using a plurality of oxygen electrodes formed on the same glass substrate 9. For example, in the structure shown in FIG. 11B, one immobilizing film 17A immobilizes glucose oxidase and the other immobilizing film 17B immobilizes glutamate oxidase. Instead of forming a plurality of oxygen electrodes on the same substrate, a plurality of independent oxygen electrodes with different immobilized bio-substance may be bonded at their side walls as indicated by a broken line in FIG. 11B.

FIG. 11C shows a structure where two biosensors such as shown in FIG. 11B are formed on both sides of a single glass substrate. Instead of forming two oxygen electrodes on both sides of a single glass substrate, the glass substrates 9A and 9B of two oxygen electrodes may be bonded. The glass substrates may be bonded together, for example, with epoxy resin.

Figure 11D:
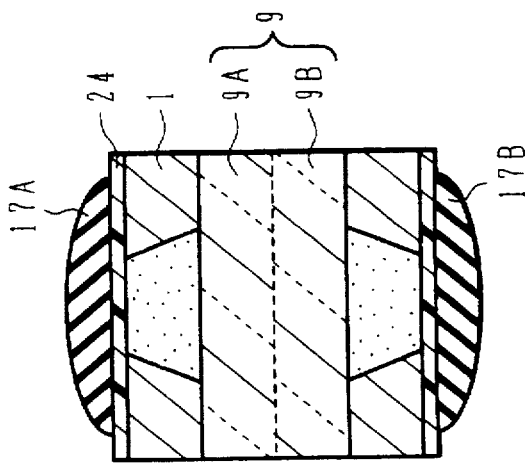

As shown in FIG. 11D, a biosensor may be housed in a tube 40 made of, for example, silicone resin in order to reinforce it. In FIG. 11D, although a biosensor of the type shown in FIG. 11A is housed, other biosensors such as shown in FIGS. 11B and 11C may be housed in a tube.

When the size of an oxygen electrode is reduced, it may be easily broken by a stress applied to the pads. For performing measurement, it is necessary to derive lead wires from the pads and it becomes of problem how to avoid the stress to be applied to the pads.

FIGS. 12A and 12B briefly show the structure of an oxygen electrode according to another embodiment of the invention. FIG. 12A is a plan view of the oxygen electrode, and FIG. 12B is a partially broken plan view thereof.

In FIG. 12A, the proximal end portion of a sensor chip 102 is covered with a resin molded structure 126 from which a pair of lead plates 115a and 115b protrudes where the resin molded structure 126 is equivalent to and serves the purpose of an insulating mold member.

When in use, the lead plate pair 115a, 115b is connected to an external circuit, and the sensor chip 102 is immersed in liquid to measure an oxygen concentration of the liquid. The resin molded structure 126 supports the sensor chip and provides an insulating surface convenient for use. A tester may grip the resin molded structure 126 and/or the lead plates 115a and 115b to handle the oxygen electrode, so that unnecessary stress will not be applied to the sensor chip.

FIG. 12B is a partially broken plan view of the oxygen electrode shown in FIG. 12A, with the upper portion of the resin molded structure 126 being removed. The upper surface of the sensor chip 102 is covered with an oxygen permeable film 114. Provided under the oxygen permeable film 114 are the cathode, anode, their leads, electrolyte for electrical conduction between the cathode and anode, and the like. At the area lower than the oxygen permeable film 114 as viewed in FIG. 12B, connection pads PA and PK are formed. The lead plates 115a and 115b are connected to the upper surfaces of the connection pads PA and PK. The connection pad PA and lead plate 115a are electrically connected by conductive material 122a such as silver paste. Similarly, the connection pad PK and lead plate 115b are electrically connected by conductive material 122b.

The lead plates 115a and 115b as well as the sensor chip 102 are fixedly mounted in the resin molded structure 126 which has a sufficient mechanical strength. Even if some stress is applied to the resin molded structure 126, it is absorbed by the resin molded structure 126 and is not applied directly to the sensor chip 102. Accordingly, even if the sensor chip 102 uses fragile material such as a silicon substrate and a glass substrate, it can be prevented from being broken. A manufacturing method of an oxygen electrode according to another embodiment will be described next.

Figure 13A:
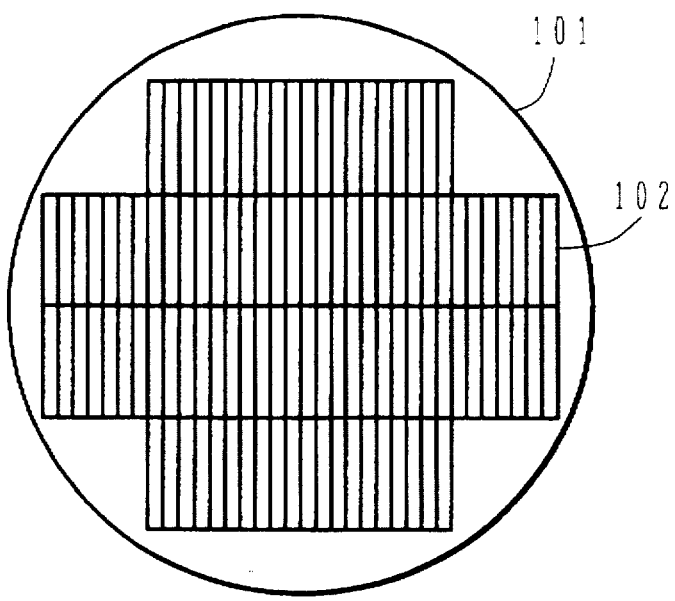

FIGS. 13A and 13D show a wafer and a sensor chip. In this embodiment, a silicon wafer 101 is used for the manufacture of oxygen electrodes. The silicon wafer 101 is, for example, a 3-inch wafer on which 108 sensor chips 102 can be fabricated at the same time.

Figure 13B:
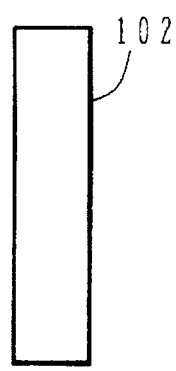

FIG. 13B shows a single sensor chip 102 corresponding to one chip 102. In the succeeding drawings, although only one chip 102 is shown, practically a number of chips are fabricated on the wafer 101 at the same time. The thickness of the silicon wafer 101 is 400 μm for example.

Figure 14A:
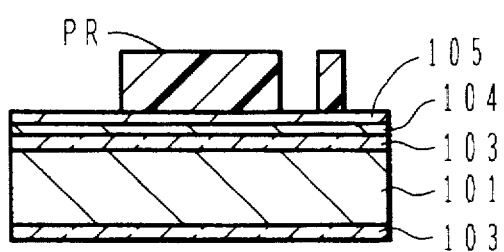

As shown in FIG. 14A, a thermally oxidized film 103 of about 1 μm thick is formed on the silicon substrate 101 through wet thermal oxidation for about 200 minutes at about 1000° C.

On one surface of the silicon substrate 101, a chromium layer 104 as an underlying layer is vapor deposited in vacuum to a thickness of about 40 nm through resistance heating. Next, a gold layer 105 of about 200 nm thick is also vapor deposited in a vacuum atmosphere through resistance heating.

On the surface of the gold layer 105, a positive type photoresist layer (OFPR-5000 manufactured by Tokyo Ohka Kogyo Co., Ltd.) is spin coated, and pre-baked for 3 minutes at 80° C. Thereafter, the photoresist layer is exposed and developed to form a photoresist pattern PR as an etching mask.

Figure 14C:
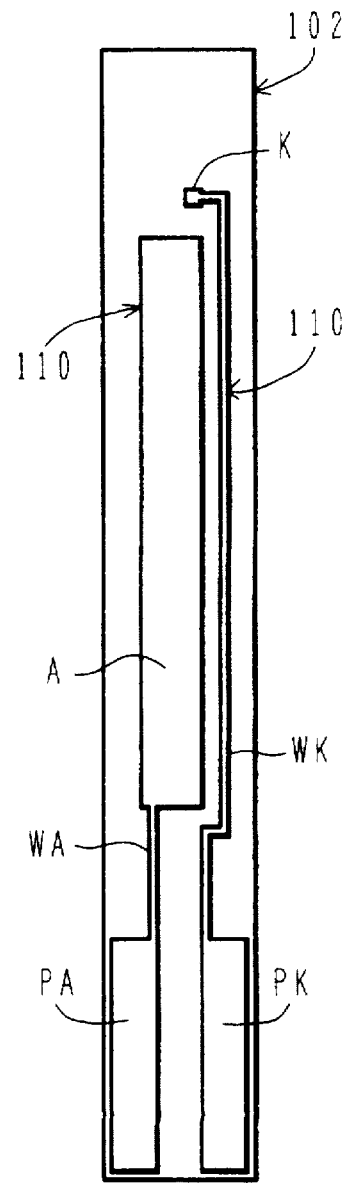
Figure 14B:
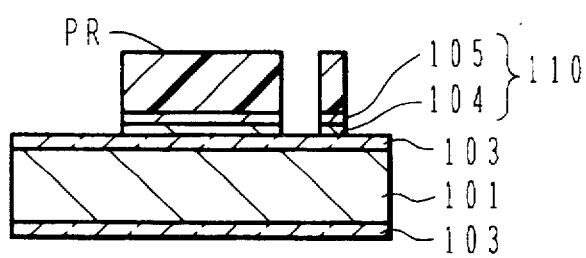

As shown in FIG. 14B, by using the photoresist pattern PR as an etching mask, the gold layer 105 and chromium layer 104 are etched. The gold layer 105 is etched by etchant of $I_2$ 1 g and KI 4 g dissolved in water 40 ml. The chromium layer 104 is etched by etchant of NaOH 0.5 g and $K_3Fe(CN)_6$ 1 g mixed with water 4 ml. After the etching, the photoresist pattern PR is removed by using acetone to obtain a conductive pattern 110.

FIG. 14C shows the shape of the conductive pattern 110 which includes two electrode sets. One electrode set includes a cathode K, a cathode lead wire WK, and a cathode connection pad PK, and the other electrode set includes an anode A, an anode lead wire WA, and an anode connection pad PA.

Figure 15A:
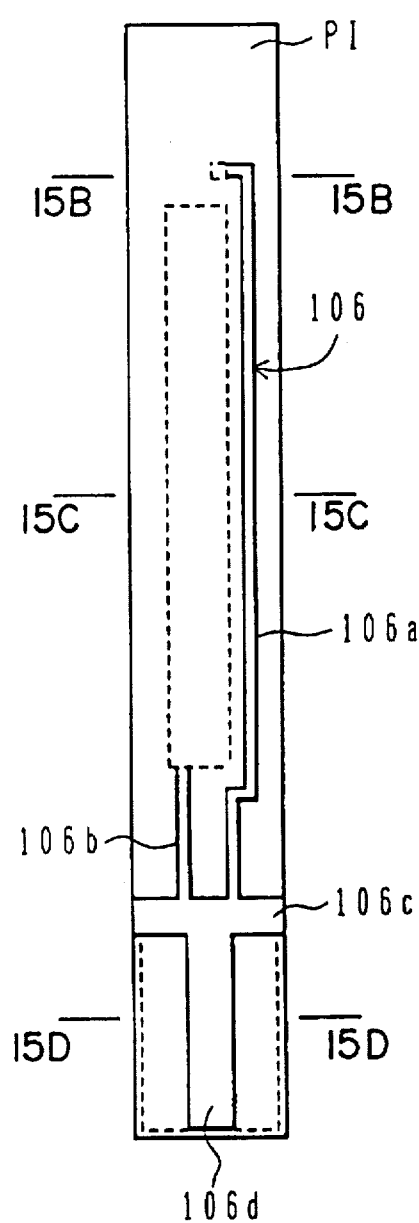

As shown in FIG. 15A, on the silicon substrate with the conductive pattern, photosensitive polyimide liquid (Photoneece (product name UR-3140), manufactured by Toray Industries Inc.) is spin coated for 30 seconds at a revolution speed of 2200 rpm, and pre-baked for 90 minutes at 80° C. A pattern such as shown in FIG. 15A is exposed on the photosensitive polyimide layer PI. As compared to the pattern shown in FIG. 14C, the photosensitive polyimide pattern PI is not formed on the cathode K and anode A, but is formed on the cathode wiring lead WK and anode wiring lead WA as patterns 106a and 106b, and between the anode connection pad PA and cathode connection pad PK as a pattern 106d. The photosensitive polyimide pattern PI further includes a lateral pattern 106c at an interconnecting region between the anode and cathode connection pads PA and PK and the anode and cathode wiring leads WA and WK.

The polyimide layer PI is developed with developing liquid (DV-605 manufactured by Toray Industries Inc.), and the substrate is rinsed three times in isopropyl alcohol. The polyimide pattern 106 is cured by baking for 30 minutes at 150° C., 30 minutes at 200° C., and for 1 hour at 300° C.

Figure 15B:
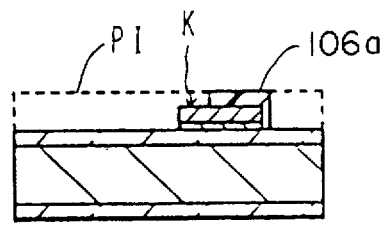

FIG. 15B is a cross sectional view taken along line B—B in FIG. 15A. As seen from FIG. 15B, the polyimide pattern 106a is not formed on the cathode K.

Figure 15C:
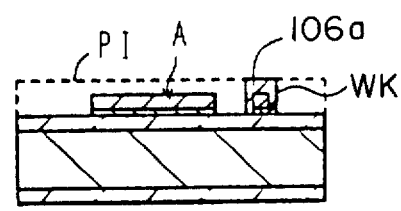
Figure 15D:
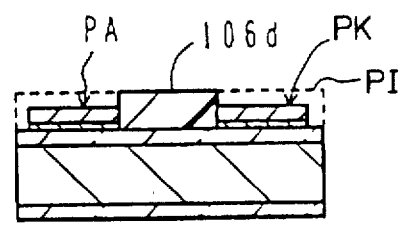

FIGS. 15C and 15D are cross sectional views taken along lines C—C and D—D in FIG. 15A. The cathode wiring lead WK is covered with the polyimide pattern 106a. The anode A, pads PA and PK are not covered with the polyimide pattern but are exposed. The space between the anode and cathode connection pads PA and PK is filled with the polyimide pattern 106d.

The polyimide bank 106d between the pads prevents a flow of conductive paste used when the Lead frame and pads are connected, and thus a short circuit between pads can be prevented.

Steps between the pads can also be alleviated by the polyimide bank 106d.

The lateral polyimide bank 106c (FIG. 15A) traversing the anode and cathode wiring leads is effective for preventing a short circuit between the pads and a defect of the oxygen electrode connection region otherwise caused by impregnation of water into the sensor chip.

Figure 16A:
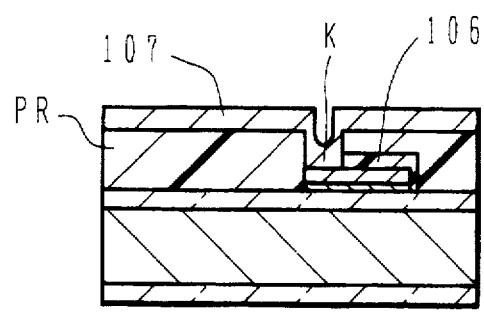
Figure 16B:
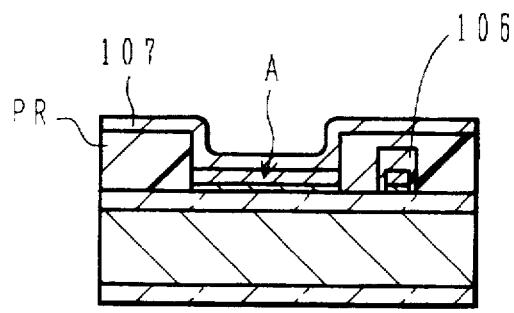

FIGS. 16A and 16B illustrate the process of forming a silver layer on the cathode and anode. FIG. 16A is a cross sectional diagram showing the region around the cathode, and FIG. 16B is a cross sectional diagram showing the region around the anode.

First, positive type photoresist (OFPR-5000 manufactured by Tokyo Ohka Kogyo Co., Ltd.) is spin coated over the whole surface of the substrate, and pre-baked for 30 minutes at 80° C. Thereafter, the positive type photoresist layer is selectively exposed, immersed in toluene for 5 minutes at 30° C., and developed after it is post-baked for 10 minutes at 80° C. Windows exposing the anode and cathode are therefore formed. A silver layer 107 is vapor deposited in vacuum through resistance heating on the photoresist pattern PR with the windows.

Thereafter, the positive type photoresist layer PR is removed by using acetone to lift off the silver layer 107 thereon and leave only the silver layer on the cathode and anode.

Figure 17A:
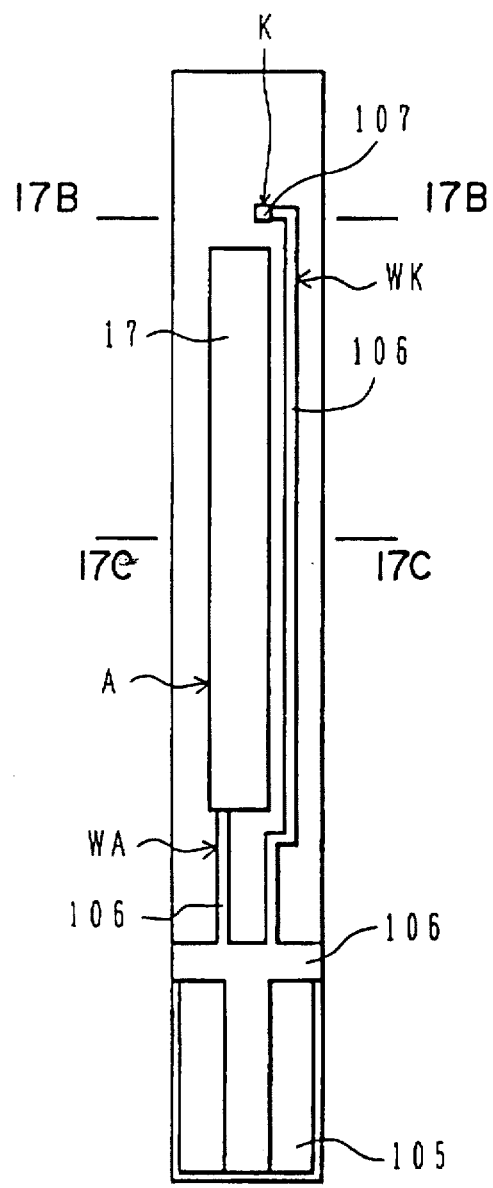
Figure 17B:
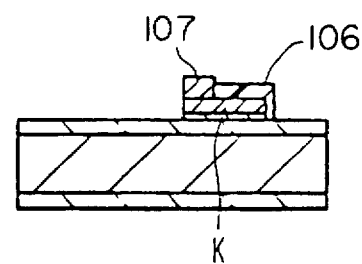
Figure 17C:
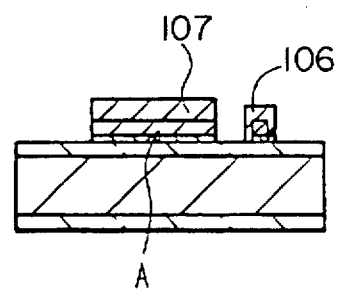

FIGS. 17A to 17C show the sensor chip after the silver layer pattern 107 was formed. FIG. 17A is a plan view of the sensor chip, and FIGS. 17B and 17C are cross sectional views taken along lines B—B and C—C in FIG. 17A. The silver layer 107 is formed only on the cathode K and anode A. The cathode wiring lead WK connected to the cathode and the anode wiring lead WA connected to the anode are covered with the polyimide film 106, as described above.

Figure 18A:
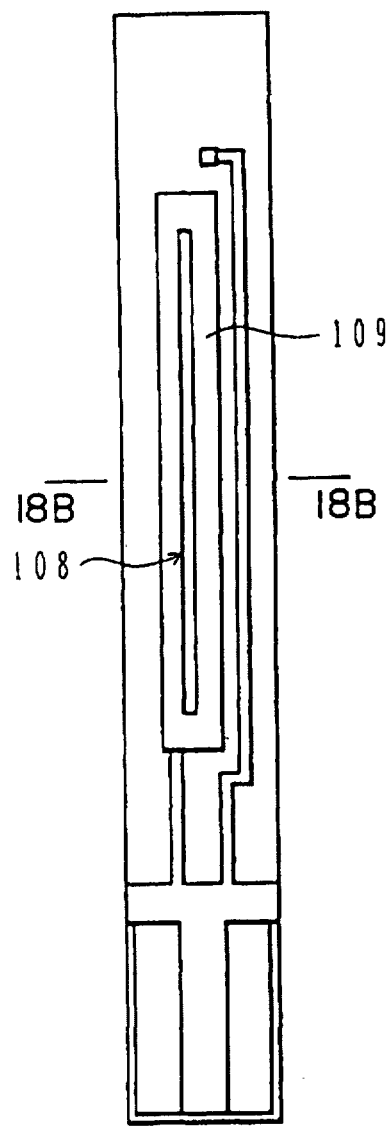
Figure 18B:
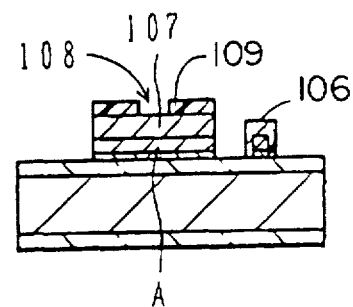

FIGS. 18A and 18B illustrate the processes of forming a water repellent film 109 on the anode A. For example, on the whole surface of the substrate, negative type photoresist (OMR-83 manufactured by Tokyo Ohka Kogyo Co., Ltd.) is spin coated. The area of the negative photoresist layer other than an area in a slit shape corresponding in position to the central area of the anode is exposed, and the negative photoresist layer is developed to form a water repellent film 109 having a slit 108 on a central portion of the anode.

The water repellent film 109 covers the anode electrode, and the anode is exposed only through the central slit 108 of the water repellent film 109, to define the contact area between the anode and an electrolyte layer to be later formed on the anode. With this configuration, silver becomes hard to be deteriorated and a stabilizing time at the initial stage can be shortened.

Figure 19A:
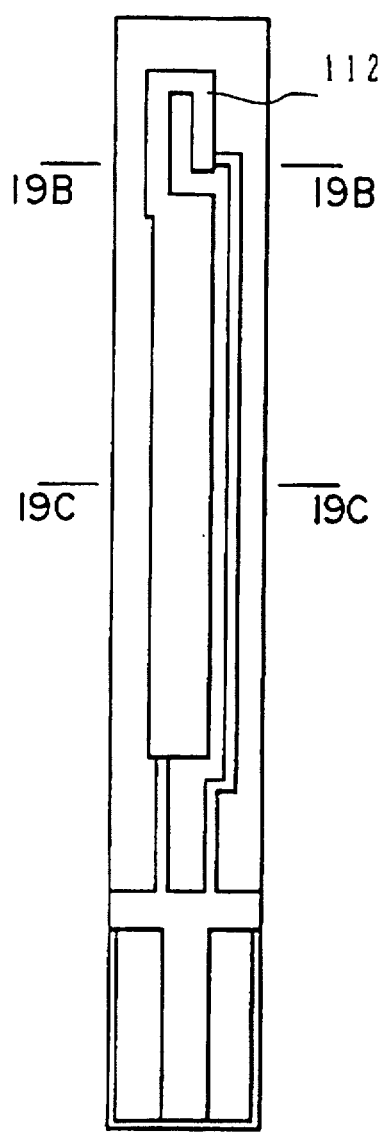
Figure 19B:
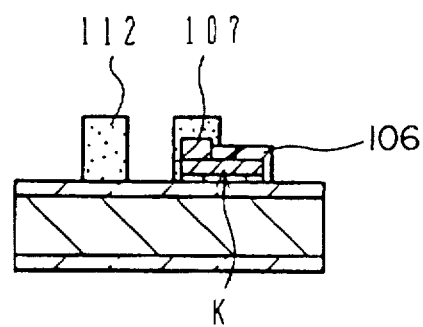
Figure 19C:
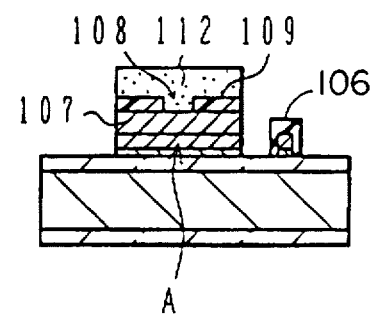

As shown in FIGS. 19A to 19C, an electrolyte layer 112 is formed on the cathode K, anode A, and a region connecting the cathode and the anode by means of screen printing. FIG. 19A is a plan view of the sensor chip, and FIGS. 19B and 19C are cross sectional views taken along lines B—B and C—C in FIG. 19A.

The electrolyte layer 112 is made of principal material of powdered potassium chloride or sodium chloride added with pH adjusting material and binder. For example, the pH adjusting material may be tris-hydroxymethyl aminomethane, glycine, phosphate, citrate, acetate, borate, or the like. The binder may be polyvinyl pyrrolidone dissolved in hexanol solution. After an electrolyte layer made of such materials is formed by screen printing, solvent is vaporized to form the solid electrolyte layer 112.

As shown in FIG. 20A, after a protective layer 113 is formed covering the pads, an oxygen permeable film 114 is coated over the whole surface of the substrate. The protective film may be formed, by screen printing Dotite XB-801 manufactured by Fujikura Kasei Co., Ltd. and baking it for about 20 minutes at 80° C. The oxygen permeable film may use silicone resin (SE9176 manufactured by Toray Dow Corning Silicone Co., Ltd). Such silicone resin is spin coated on the whole surface of the substrate and subjected to a heat curing process in a humidified constant temperature oven for 60 minutes at 80° C.

Humidification is performed to enhance curing. This may be achieved by placing a Petri dish containing water or a beaker containing water in a constant temperature oven.

Thereafter, the protective film 113 covering the pad regions is removed with tweezers or the like. At this time, a portion of the oxygen permeable film on the protective film 113 is also removed. The pad region is therefore exposed.

FIGS. 20B and 20C are cross sectional views taken along lines B—B and C—C in FIG. 20A. The oxygen permeable film 114 covers the whole surface of the substrate excepting the pad region.

Thereafter, as shown in FIG. 13A, the semiconductor wafer 101 is cut with a dicing saw into each separated chip 102. Conventionally, each chip of this state has been used as an oxygen electrode.

Figure 21:
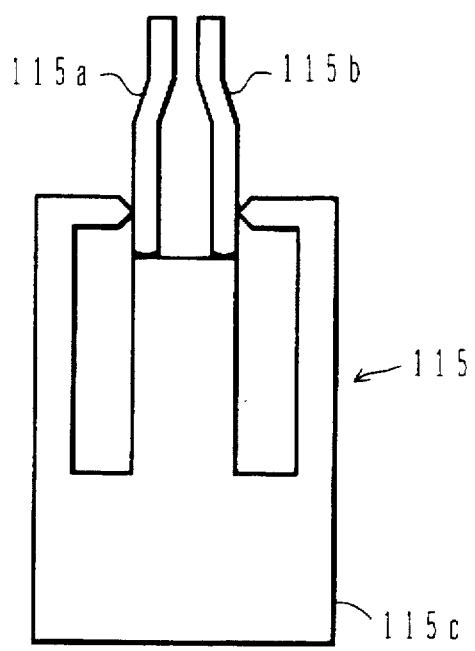
FIG. 21 is a plan view showing a lead frame used for the fabrication of the oxygen electrode shown in FIGS. 12A and 12B.

FIG. 21 shows an example of the structure of a lead frame. The lead frame 115 is made of, for example, a 42 alloy (42% nickel-iron) plate of about 200 μm thick. Two lead plates 115a and 115b are formed at the upper area and supported by a lower support member 115c. The connection areas between the lead plates 115a and 115b and the support member 115c are made narrow so that these areas can be cut easily with a punching machine.

Figures 22A, 22B:
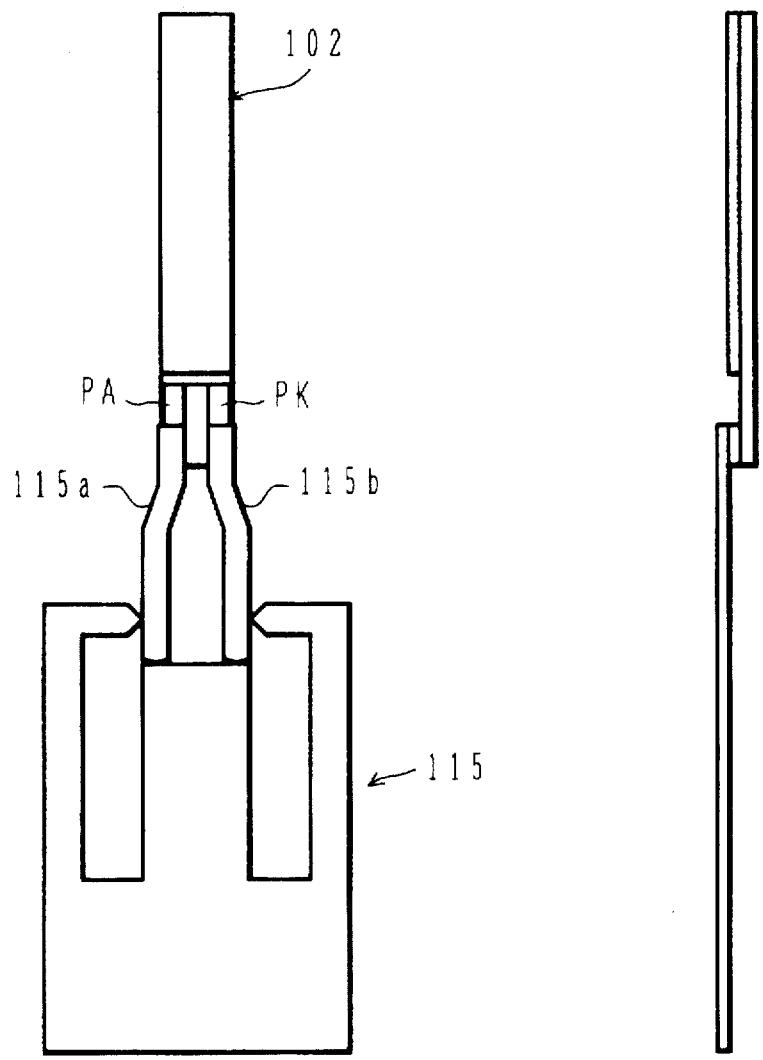
FIGS. 22A and 22B are a plan view and a side view showing the lead frame fixed to a sensor chip.

FIGS. 22A and 22B show the connection state of the lead frame 115 on the sensor chip 102. The end portions of the lead plates 115a and 115b of the lead frame 115 are coupled to the lower portions of the pads PA and PK with an adhesive layer.

In this case, the upper portions of the pads PA and PK are required to be exposed. The adhesive may be XN-5831-1 manufactured by Bellnox Corp.

After the lead frame is bonded to the pads with adhesive, a baking process is performed, for example, for about 15 minutes at 150° C., to cure the adhesive. In this manner, an integrated structure of the sensor chip 102 and lead frame 115 can be obtained. In this state, the pads PA and PK on the sensor chip 102 and the lead frame 115 are electrically isolated.

Figures 23A, 23B:
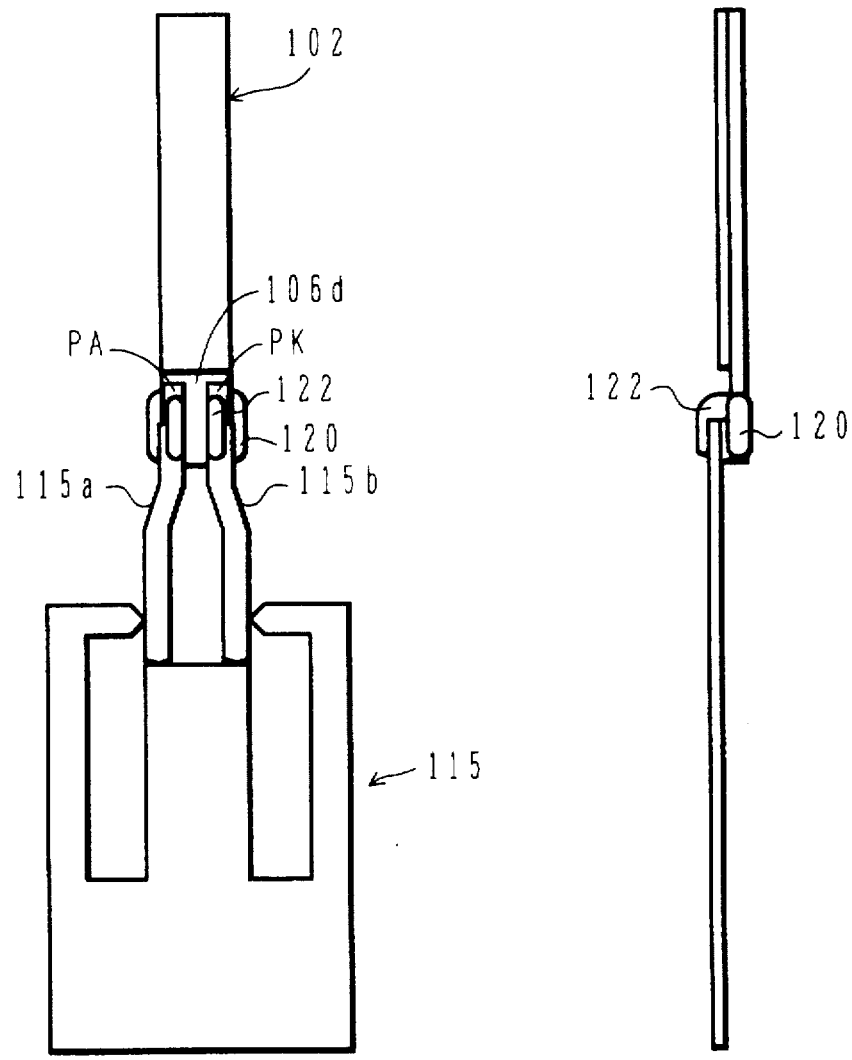
FIGS. 23A and 23B are a plan view and a side view showing the lead frame fixed and electrically connected to a sensor chip.

As shown in FIGS. 23A and 23B, the side walls of the sensor chip 102 where the connection pads are formed are coated with silicone varnish (KR-5240 manufactured by Shin-Etsu Chemical Co., Ltd) to form varnish layers 120 which increase the dielectric strength at the side walls of the silicon sensor chip 102.

Thereafter, silver paste is partially coated so as to connect the anode and cathode connection pads PA and PK respectively to the corresponding lead plates 115a and 115b of the lead frame and form a silver paste layer 122. During this process, flow of the silver paste is restricted by the polyimide layer 106d between the pads and the varnish layers 120 on the chip side walls.

As shown in FIGS. 24A and 24B, an insulating layer 124 is formed covering the connection area with the silver paste and its peripheral area. The insulating film 124 is made of insulating material having excellent water-proof properties and ability to be in tight contact. For example, Worldlock manufactured by Kyoritsu Chemical Co., Ltd is coated and cured by applying ultraviolet rays at 100 mW/cm$^2$ for 20 seconds.

This insulating layer ensures electrical isolation. Depending upon the application field, it may be omitted and the sensor chip without the insulating layer may be molded directly.

FIGS. 25A and 25B illustrate the process of molding the connection area between the sensor chip and lead frame with insulating resin. A resin molded structure 126 is formed, for example, by using epoxy-based resin having high waterproof properties and ability to form a highly tight contact. The resin molded structure 126 may include a suitable filler.

The resin mold structure 126 fixes the sensor chip and lead frame and provides definite relative positions of the sensor chip and lead frame. Stress applied to the lead frame is absorbed by the resin molded structure 126 so that the sensor chip at the local connection area is prevented from being applied with stress. Electrical connection from the pads PA and PK on the sensor chip to the lead plates 115a and 115b is also ensured.

Thereafter, the support member 115c of the lead frame is cut from the lead plates 115a and 115b to obtain an oxygen electrode such as shown in FIG. 12A.

The compact oxygen electrode fabricated in the above manner is immersed overnight in water at a room temperature or placed in an autoclave furnace at 120° C. for 15 minutes with a gauge pressure of 1.2 atmospheric pressure, to thereby make the electrode practically usable. Specifically, water or water vapor is supplied to the electrolyte layer so that the essential function of the oxygen electrode can be matured.

In the embodiment described above, the thermally oxidized film is formed on the surface of the silicon substrate, and the anode and cathode electrodes are formed on the thermally oxidized film. An aspect of this embodiment resides in that the lead plates for the connection to an external circuit are connected to the pads for the connection to the anode and cathode electrodes and this connection area is housed in the resin molded structure. The embodiment does not specifically limit the structure of the inside of the sensor chip.

For example, the lead plates of a lead frame may be connected to the pads 8A and 8B shown in FIG. 1A, and this connection area is housed in the resin molded structure similar to this embodiment.

In this embodiment, the lead plates of a lead frame extend along the longitudinal direction of the sensor chip and protrude from the resin molded structure on the side opposite to the sensor chip. The lead plates may protrude from the resin molded structure at positions different from the side opposite to the sensor chip.

Figure 26A:
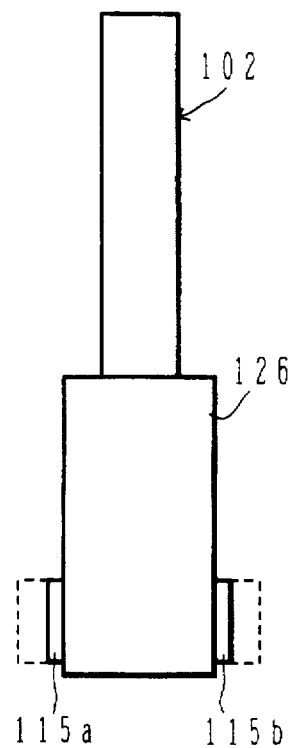
FIGS. 26A to 26C are plan views and a partially broken plan view showing structures of a compact oxygen electrode according to other embodiments of the invention.
Figure 26B:
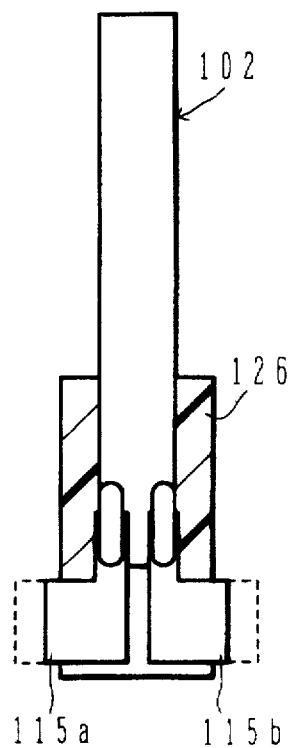
Figure 26C:
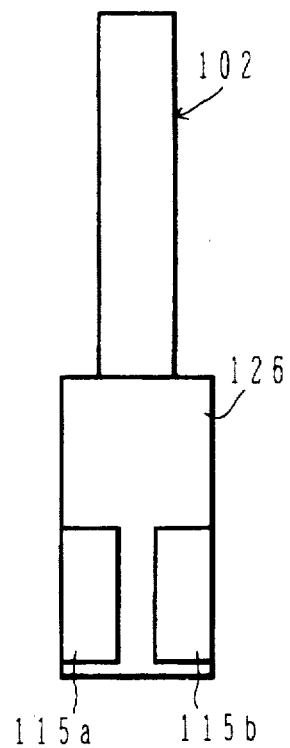

FIGS. 26A to 26C show other examples of protruding lead plates.

As shown in FIG. 26A, the lead plates 115a and 115b protrude from opposite sides of the resin molded structure 126 and extend laterally to the sensor chip 102.

FIG. 26B shows the sensor chip of FIG. 26A with the upper portion of the resin molded structure 126 removed. The lead plates 115a and 115b are generally of an L-character shape which are bent at the positions under the connection area to the pads and extended laterally. The length of the laterally extending lead plate is determined as desired.

FIG. 26C shows a modification of the sensor chip shown in FIG. 26A. In this modification, the lead plates 115a and 115b protrude from the opposite sides of the resin molded structure 126 and then bend along the surface of the resin molded structure 126. This structure is useful when the sensor chip is plugged into a receptacle.

Figure 27A:
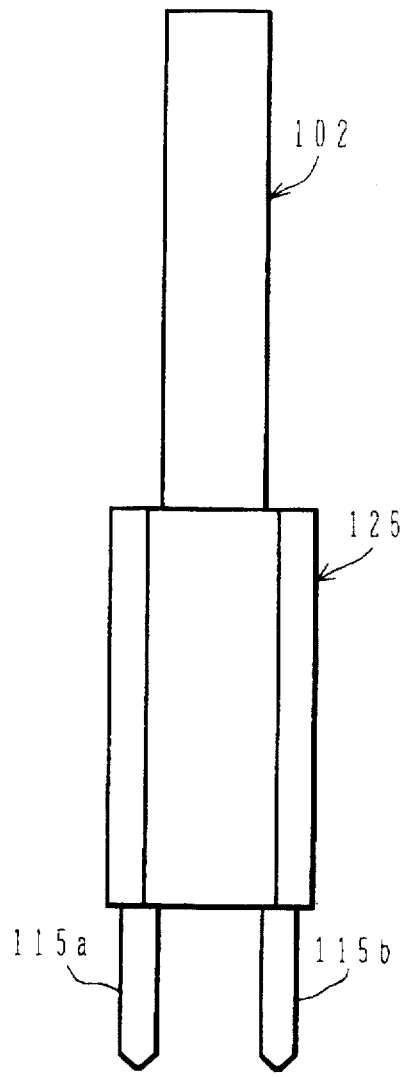
FIGS. 27A to 27D are plan views and bottom views showing the structures of compact oxygen electrodes according to other embodiments of the invention.
Figure 27B:
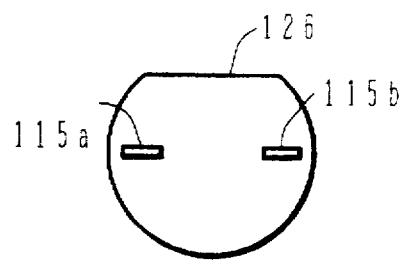

FIGS. 27A to 27D show other examples of the resin molded structure 126. In FIG. 27A and 27B, the resin molded structure 126 is generally of a cylindrical shape with a partial flat plane which prevents the sensor chip from rolling when it is placed on a surface. Also, the cut-away portion is effective to differentiate the two lead plates 115a and 115b.

Figure 27C:
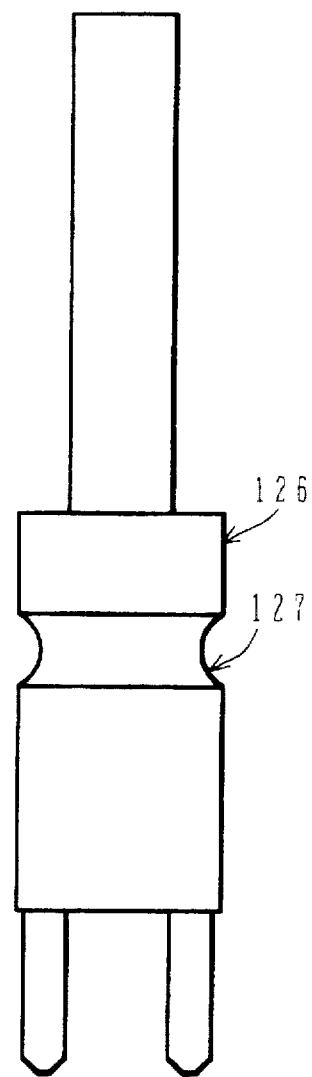
Figure 27D:
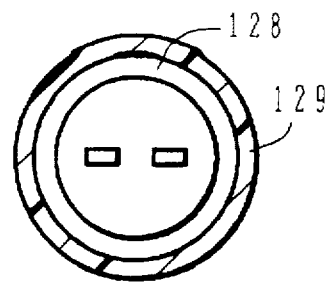

FIG. 27C shows another example of the resin molded structure. As shown, an O-ring fitting groove 127 is formed on the circumference of the resin molded structure 126. As shown in FIG. 27D, an O-ring 128 is fitted into the groove 127, and an outer sleeve 129 is fitted on the resin molded structure 126 with the O-ring 128 from the side of the lead plates 115a and 115b to engage with the O-ring 128. With this arrangement, the lead plates 115a and 115b can be sheltered from external water droplets or the like.

FIGS. 28A to 28D illustrate connections of the lead plates to the connection pads of the sensor chip.

Figure 28A:
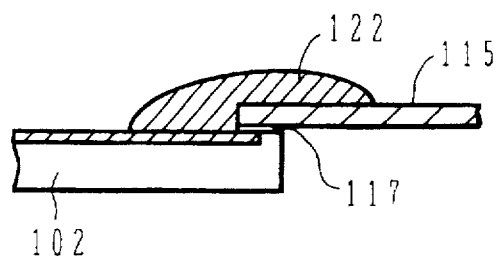
FIGS. 28A to 28D are schematic cross sectional views illustrating various connections of sensor chips, with a lead plate of lead frame.

FIG. 28A illustrates a connection of the above-described embodiment. The lead plate 115 is fixed to the surface of the sensor chip 102 by the adhesive layer 117, and electrically connected to the connection pad of the sensor chip 102 by the silver paste layer 122.

Figure 28B:
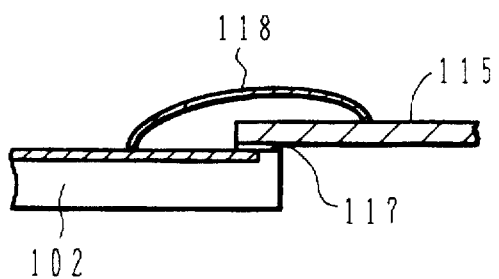

FIG. 28B illustrates a connection using a metal bonding wire 118. After the lead plate 115 is fixed to the surface of the sensor chip 102 by the adhesive layer 117, it is wire bonded by a metal wire 118 to the connection pad of the sensor chip 102.

Figure 28C:
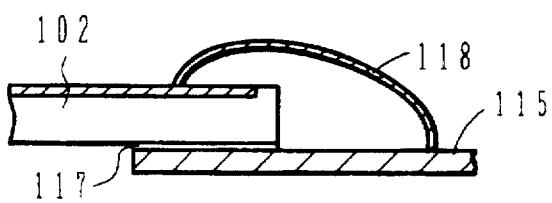

FIG. 28C illustrates a connection of the lead plate 115 to the lower surface of the sensor chip 102 by using an adhesive layer 117. In this case, since the surface of the lead plate 115 becomes more remote from the surface of the sensor chip 102, it is more preferable to connect the lead plate to the pad by a metal wire 118 than by a silver paste layer.

Figure 28D:
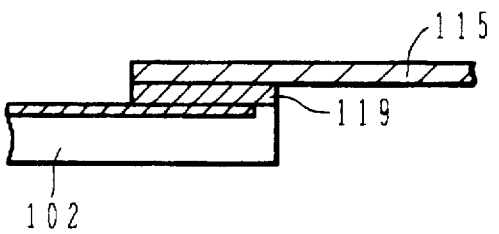

FIG. 28D illustrates a more simple connection. A conductive paste 119 is coated on the surface of the connection pad of the sensor chip 102, and the lead plate 115 is placed on this conductive plate to fix the sensor chip 102 and lead plate 115.

As described so far, the compact oxygen electrode is not used in a bare chip state, but is partially molded with resin except for the sensing portion. In this resin molded structure, the connection pads of the sensor chip are connected to the lead plates which protrude from the resin molded structure. Connection to an external circuit can be achieved reliably via the protruding lead plates without excepting any defective stress to the sensor chip.

Resin molds are widely used for semiconductor integrated circuits and the like. A resin mold used for general semiconductor devices is different from a resin mold used for compact oxygen electrodes in the following respects.

Although the semiconductor chip of a semiconductor device is completely molded in resin, at least the sensing portion of a compact oxygen electrode is required to be exposed through resin mold.

Although semiconductor devices are used under prescribed conditions, oxygen electrodes are used under various severe conditions such as in water vapor, at high temperature, and at low temperature. A rubber film or the like having gas permeability may be formed on the surface of a compact oxygen electrode. The resin mold is required to reliably seal the connection area including this rubber film.

Figure 29:
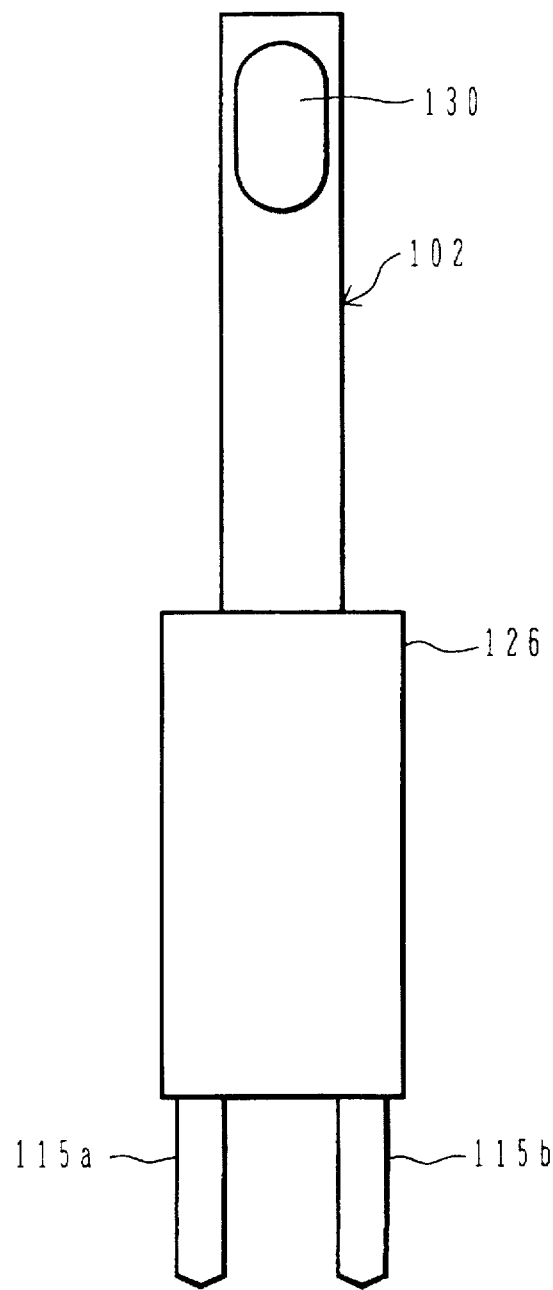
FIG. 29 is a plan view showing the structure of a biosensor according to another embodiment of the invention.

FIG. 29 shows a biosensor having an immobilizing film 130 formed at the sensing area and containing immobilized enzymes such as glucose oxidase. A sensor chip 102, a resin molded structure 126, and lead plates 115a and 115b have similar structures to the above-described embodiments. The enzyme immobilizing film 130 is formed at the position corresponding to the cathode.

This enzyme immobilizing film 130 may be formed, for example, by immersing a compact oxygen electrode sensing portion in a solution of glucose oxidase 1mg dissolved in a solution of 20 ml of bovine serum albumin 15 wt % and glutaraldehyde 5 wt %, and by drying.

Since the enzymes are immobilized, the autoclave process for activating the biosensor cannot be employed. It is therefore preferable to activate the biosensor with immobilized enzymes by immersing it in water at a room temperature for 12 hours or longer.

FIGS. 30A and 30B show another example of the structure of a biosensor. Two compact biosensors are juxtaposed and molded in the same resin molded structure 126. Four lead plates 115a to 115d are connected to the two biosensors. For example, one biosensor is formed with an enzyme immobilizing film 130a with immobilized glucose oxidase and the other biosensor is formed with an enzyme immobilizing film 130b with immobilized glutamate oxidase.

FIG. 30B shows the biosensors with the upper portion of the resin molded structure 126 being removed. The two compact oxygen electrodes 102a and 102b may be two discrete oxygen electrodes, or more preferably a chip having two oxygen electrodes collectively cut from a wafer. By using the chip with two oxygen electrodes, a composite oxygen electrode can be manufactured by processes similar to those forming a single oxygen electrode.

Figure 31A:
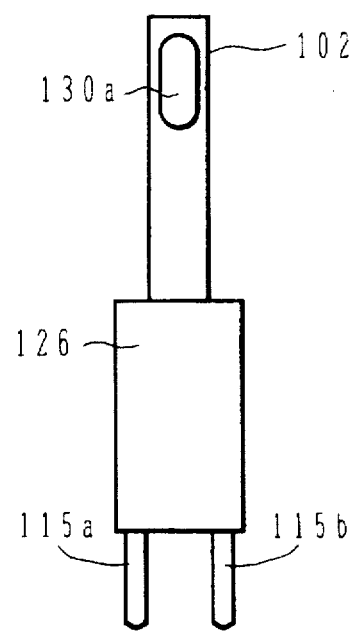
FIGS. 31A and 31B are a plan view and a side view of a biosensor according to another embodiment of the invention.
Figure 31B:
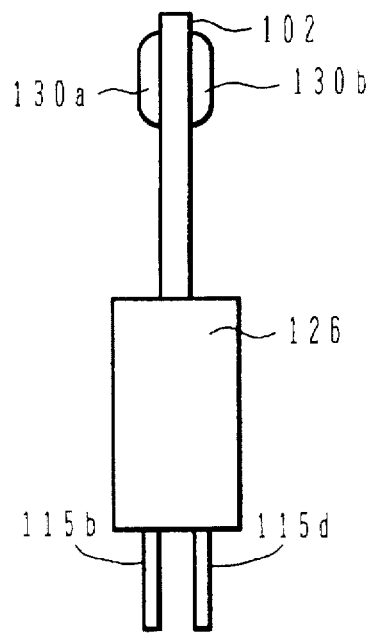

FIGS. 31A and 31B show another example of the structure of integrated biosensors. One biosensor is formed on a front surface of a chip 102, and the other biosensor is formed on the back surface thereof.

As shown in FIG. 31B, two enzyme immobilizing films 130a and 130b are formed on the front and back surfaces of the chip 102. Lead plates are also mounted on both sides of the chip. With this compact assembly of two biosensors, a variety of measurements are possible.

The structure shown in FIGS. 31A and 31B is compact and convenient for measurements, but the manufacturing process is somewhat complicated.

Figure 32:
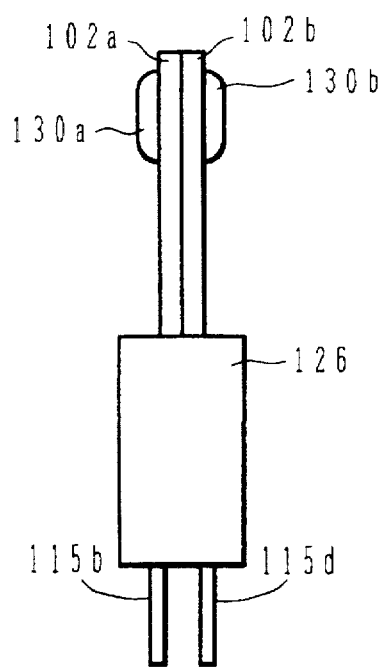
FIG. 32 is a side view of a biosensor according to another embodiment of the invention.

FIG. 32 shows another example of such an assembly which is easier to manufacture. In this example, two compact oxygen electrodes are bonded back to back and molded with the same resin molded structure 126. Enzyme immobilizing films 130a and 130b are formed on the surfaces of the oxygen electrodes to provide two types of biosensors. With this structure, an assembly similar to that shown in FIGS. 31A and 31B can be configured. Bonding the two oxygen electrodes may be made, for example, by using an epoxy-based resin.

In the above description, a 42 alloy plate of about 200 mm thick or the like is used as the material of the lead frame. The material and thickness of the lead frame are not limited thereto. For example, the thickness is not limited to about 200 mm but any other thickness may be selected as desired. Instead of a lead plate cut from a lead frame, other conductive patterns formed on a ceramic or plastic insulating substrate through screen printing may also be used. In this case, preferably this wiring pattern substrate is bonded to the back surface of the sensor chip and the pads and conductive pattern leads on the substrate are connected by bonding wires.

The present invention has been described in connection with the above embodiments. However, the invention is not limited only to the above embodiments. It is apparent to those skilled in the art that various modifications, improvements, combinations and the like can be made.

I claim:

1. An oxygen electrode comprising:
    an electrode substrate having an insulating surface;
    a first electrode member formed on the insulating surface of said electrode substrate, said first electrode member including a first electrode, a first lead wire, and a first connection pad electrically connected together;
    a second electrode member formed on the insulating surface of said electrode substrate, said second electrode member including a second electrode, a second lead wire, and a second connection pad electrically connected together;
    an electrolyte layer disposed over said electrode substrate so as to form a conductive path between the first and second electrodes;
    an oxygen permeable film disposed over said electrode substrate, covering said electrolyte layer;
    first and second lead plates each having one end directly fixed to said electrode substrate;
    a first connection member for connecting said first connection pad to said first lead plate;
    a second connection member for connecting said second connection pad to said second lead plate; and
    an insulating mold member surrounding around and fixed to said electrode substrate and covering said first and second connection pads, said each one end of said first and second lead plates, and said first and second connection members.

2. An oxygen electrode according to claim 1, wherein each of said first and second connection members includes conductive paste.

3. An oxygen electrode according to claim 2, wherein said first and second connection members include conductive paste layers disposed between said first connection pad and said first lead plate and between said second connection pad and said second lead plate.

4. An oxygen electrode according to claim 2, further comprising an insulating resin layer disposed directly on said electrode substrate between said first and second connection pads.

5. An oxygen electrode according to claim 1, wherein each of said first and second connection members includes a metal wire.

6. An oxygen electrode according to claim 5, wherein said first and second lead plates are bonded to a surface opposite to the surface of said electrode substrate with said first and second electrode members.

7. An oxygen electrode according to claim 1, further comprising an insulating resin layer disposed directly on said electrode substrate, covering a connection area between said first and second lead wires and said first and second connection pads.

8. An oxygen electrode according to claim 1, further comprising an insulating resin layer disposed directly on said electrode substrate, covering a connection area between said first and second connection pads and said first and second lead plates.

9. An oxygen electrode according to claim 1, wherein said electrode substrate has a rectangular shape having a longer side and a shorter side, and said first and second lead plates extend in the longitudinal direction of said electrode substrate.

10. An oxygen electrode according to claim 1, wherein said electrode substrate has a rectangular shape having a longer side and a shorter side, and said first and second lead plates extend in a lateral direction transverse to a longitudinal direction of said electrode substrate.

11. An oxygen electrode according to claim 1, wherein said electrode substrate has a rectangular shape having a longer side and a shorter side, and each of said first and second lead plates having a portion folded along an outer surface of said mold member.

12. An oxygen electrode according to claim 1, wherein said mold member includes a loop groove circulating around said electrode substrate.

13. An oxygen electrode according to claim 1, wherein said mold member partially has a flat surface.

14. An oxygen electrode comprising:
an electrode substrate having an insulating surface;
a first electrode member formed on the insulating surface of said electrode substrate, said first electrode member including a first electrode, a first lead wire, and a first connection pad electrically connected together;
a second electrode member formed on the insulating surface of said electrode substrate, said second electrode member including a second electrode, a second lead wire, and a second connection pad electrically connected together;
an electrolyte layer disposed over said electrode substrate so as to form a conductive path between the first and second electrodes;
an oxygen permeable film disposed over said electrode substrate, covering said electrolyte layer;
first and second lead plates each having one end directly fixed to said electrode substrate;
a first connection member for connecting said first connection pad to said first lead plate;
a second connection member for connecting said second connection pad to said second lead plate; and
an insulating mold member fixed to said electrode substrate and covering said first and second connection pads, said each one end of said first and second lead plates, and said first and second connection members, the insulating mold member having a sufficient mechanical strength to absorb stress applied thereto.

15. An oxygen electrode according to claim 14, wherein each of said first and second connection members includes conductive paste.

16. An oxygen electrode according to claim 15, wherein said first and second connection members include conductive paste layers disposed between said first connection pad and said first lead plate and between said second connection pad and said second lead plate.

17. An oxygen electrode according to claim 15, further comprising an insulating resin layer disposed directly on said electrode substrate between said first and second connection pads.

18. An oxygen electrode according to claim 14, wherein each of said first and second connection members includes a metal wire.

19. An oxygen electrode according to claim 18, wherein said first and second lead plates are bonded to a surface opposite to the surface of said electrode substrate with said first and second electrode members.

20. An oxygen electrode according to claim 14, further comprising an insulating resin layer disposed directly on said electrode substrate, covering a connection area between said first and second lead wires and said first and second connection pads.

21. An oxygen electrode according to claim 14, further comprising an insulating resin layer disposed directly on said electrode substrate, covering a connection area between said first and second connection pads and said first and second lead plates.

22. An oxygen electrode according to claim 14, wherein said electrode substrate has a rectangular shape having a longer side and a shorter side, and said first and second lead plates extend in the longitudinal direction of said electrode substrate.

23. An oxygen electrode according to claim 14, wherein said electrode substrate has a rectangular shape having a longer side and a shorter side, and said first and second lead plates extend in a lateral direction transverse to a longitudinal direction of said electrode substrate.

24. An oxygen electrode according to claim 14, wherein said electrode substrate has a rectangular shape having a longer side and a shorter side, and each of said first and second lead plates having a portion folded along an outer surface of said mold member.

25. An oxygen electrode according to claim 14, wherein said mold member includes a loop groove circulating around said electrode substrate.

26. An oxygen electrode according to claim 14, wherein said mold member partially has a flat surface.

27. An oxygen electrode comprising:
an electrode substrate having an insulating surface;
a first electrode member formed on the insulating surface of said electrode substrate, said first electrode member including a first electrode, a first lead wire, and a first connection pad electrically connected together;
a second electrode member formed on the insulating surface of said electrode substrate, said second electrode member including a second electrode, a second lead wire, and a second connection pad electrically connected together;
an electrolyte layer disposed over said electrode substrate so as to form a conductive path between the first and second electrodes;
an oxygen permeable film disposed over said electrode substrate, covering said electrolyte layer;
first and second lead plates having each one end directly fixed to said electrode substrate;
a first connection member for connecting said first connection pad to said first lead plate;
a second connection member for connecting said second connection pad to said second lead plate; and
an insulating mold member fixed to said electrode substrate and covering said first and second connection pads, said each one end of said first and second lead plates, and said first and second connection members, said first and second lead plates having portions extending outside of said insulating mold member;
wherein the mold member or the lead plates can be gripped to handle the oxygen electrode, while the electrode substrate is protected from stress.

28. An oxygen electrode according to claim 27, wherein each of said first and second connection members includes conductive paste.

29. An oxygen electrode according to claim 28, wherein said first and second connection members include conductive paste layers disposed between said first connection pad and said first lead plate and between said second connection pad and said second lead plate.

30. An oxygen electrode according to claim 28, further comprising an insulating resin layer disposed directly on said electrode substrate between said first and second connection pads.

31. An oxygen electrode according to claim 27, wherein each of said first and second connection members includes a metal wire.

32. An oxygen electrode according to claim 31, wherein said first and second lead plates are bonded to a surface opposite to the surface of said electrode substrate with said first and second electrode members.

33. An oxygen electrode according to claim 27, further comprising an insulating resin layer disposed directly on said electrode substrate, covering a connection area between said first and second lead wires and said first and second connection pads.

34. An oxygen electrode according to claim 27, further comprising an insulating resin layer disposed directly on said electrode substrate, covering a connection area between said first and second connection pads and said first and second lead plates.

35. An oxygen electrode according to claim 27, wherein said electrode substrate has a rectangular shape having a longer side and a shorter side, and said first and second lead plates extend in the longitudinal direction of said electrode substrate.

36. An oxygen electrode according to claim 27, wherein said electrode substrate has a rectangular-shape having a longer side and a shorter side, and said first and second lead plates extend in a lateral direction transverse to a longitudinal direction of said electrode substrate.

37. An oxygen electrode according to claim 27, wherein said electrode substrate has a rectangular shape having a longer side and a shorter side, and each of said first and second lead plates having a portion folded along an outer surface of said mold member.

38. An oxygen electrode according to claim 27, wherein said mold member includes a loop groove circulating around said electrode substrate.

39. An oxygen electrode according to claim 27, wherein said mold member partially has a flat surface.

* * * * *